US008618051B2

(12) United States Patent
Buchanan et al.

(10) Patent No.: US 8,618,051 B2
(45) Date of Patent: Dec. 31, 2013

(54) VESICULINS

(75) Inventors: Christina Maree Buchanan, Auckland (NZ); Garth James Smith Cooper, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 260 days.

(21) Appl. No.: 12/848,835

(22) Filed: Aug. 2, 2010

(65) Prior Publication Data

US 2010/0311672 A1 Dec. 9, 2010

Related U.S. Application Data

(63) Continuation of application No. 11/912,111, filed as application No. PCT/NZ2006/000078 on Apr. 20, 2006, now abandoned.

(60) Provisional application No. 60/673,537, filed on Apr. 20, 2005.

(51) Int. Cl.
*A61K 38/28* (2006.01)
*C07K 14/65* (2006.01)

(52) U.S. Cl.
USPC .......................................... 514/8.6; 530/303

(58) Field of Classification Search
None
See application file for complete search history.

(56) References Cited

U.S. PATENT DOCUMENTS

| 3,773,919 | A | 11/1973 | Boswell et al. |
| 4,767,628 | A | 8/1988 | Hutchinson |
| 4,816,567 | A | 3/1989 | Cabilly et al. |

FOREIGN PATENT DOCUMENTS

| EP | 0 332 435 | 9/1989 |
| JP | 2000-191697 | 7/2000 |
| WO | WO 93/08826 | 5/1993 |
| WO | WO 93/20836 | 10/1993 |
| WO | WO 94/15587 | 7/1994 |
| WO | WO 00/78805 | 12/2000 |
| WO | WO 2006/026355 | 3/2006 |

OTHER PUBLICATIONS

Altschul et al. (1997) "Gapped BLAST and PSI-BLAST: A New Generation of Protein Database Search Programs," *Nuc. Acids Res.* 25(17):3389-3402.
Bairoch et al. (1994) "Prosite: Recent Developments," *Nuc. Acids Res.* 22:3583-3589.
Baxevanis, A.D. (2001) "The Molecular Biology Database Collection: An Updates Compilation of Biological Database Resources," *Nuc. Acids Res.* 29(1):1-10.
Binoux, M. (1995) "The IGF System in Metabolism Regulation," *Diabete et Metabolism* 21(5):330-337.
Bolton et al. (1962) "A General Method for the Isolation of RNA Complementary to DNA," *Proc. Nat. Acad. Sci. USA* 48:1390-1397.
Bowie et al. (Mar. 1990) "Deciphering the Message in protein Sequences: Tolerance to Amino Acid Substitutions," *Science* 247:1306-1310.
Buck et al. (1982) "Monoclonal Antibodies Specific for Cell Culture Mycoplasmas," *In Vitro* 18:377-381.
Burgisser et al. (Jan. 1991) "Mutants of Human Insulin-Like Growth Factor II with Altered Affinities for the Type 1 and Type 2 insulin-Like Growth Factor Receptor," *J. Biol. Chem.* 266(2):1029-1033.
Buzayan et al. (Sep. 1986) "Non-Enzymatic Cleavage and Ligation of RNAs Complementary to a Plant Virus Satellite RNA," *Nature* 323:349-353.
Chang et al. (Nov. 1981) "Differential Assay of Arylsulfatase A and B Activities: A Sensitive Method for Cultured Human Cells," *Anal. Biochem.* 117(2):382-389.
Cockett et al. (1990) *Bio/Technology* 8:662-667.
Daughaday et Al. (Jun. 1993) "Serum 'Big Insulin-like Growth Factor II' from Patients with Tumor Hypoglycemia Lacks Normal E-Domain O-Linked Glycosylation, a Possible Determinant of Normal Propeptide Processing," *Proc. Nat. Acad. Sci. USA* 90:5823-5827.
Daughaday et al. (1988) *New Eng. J. Med.* 319:1434-1441.
Deutscher (1990) "Guide to Protein Purification," *Methods Enzymol.* 182:83-89.
Dickson et al. (Jun. 2001) "Differential Activation of Protein Kinase B and p70$^{S6K}$ by Glucose and Insulin-Like Growth Factor 1 in Pancreatic β-Cells (INS-1)," *J. Biol. Chem.* 276:21110-21120.
Falquet et al. (2002) "The PROSITE Database. Its Status in 2002," *Nuc. Acids Res.* 30(1):235-238.
Feng et al. (1987) "Progressive Sequence Alignment as a Prerequisite to Correct Phylogenetic Trees," *J. Mol. Evol.* 25:351-360.
Flier et al. (Jun. 2001) "Evidence for a Circulating Islet Cell Growth Factor in Insulin-Resistant States," *Proc. Nat. Acad. Sci. USA* 98(13):7475-7480.
Freshney, R.I. (1987) *Culture of Animal Cells*, 2$^{nd}$ ed., Wiley-Liss pub., pp. 6-13 and 126-137.
Giesen et al. (1998) "A Formula for Thermal Stability ($T_m$) Prediction of PNA/DNA Duplexes," *Nuc. Acids Res.* 26(21):5004-5006.
Gill et al. (1996) "Engineering the C-Region of Human Insulin-Like Growth Factor-1: Implications for Receptor Binding," *Protein Eng.* 9(11):1011-1019.
Gowan et al. (1987) "Purification and Characterization of a Unique High Molecular Weight Form of Insulin-Like Growth Factor II," *Endocrinology* 121:449-458.
Hampton et al. (Nov. 1989) "Purification and Characterization of an Insulin-Like Growth Factor II Variant from Human Plasma," *J. Biol. Chem.* 264:19155-19160.
Harlow et al. (1987) *Antibodies: A Laboratory Manual*, pp. 52-137.
Haselbacher et al. (1982) "Evidence for Two Species of Insulin-Like Growth Factor II (IGF II and 'big' IGF II) in Human Spinal Fluid," *Endocrinology* 110:1822-1824.

(Continued)

*Primary Examiner* — Christine J Saoud
(74) *Attorney, Agent, or Firm* — Lathrop & Gage LLP

(57) ABSTRACT

The inventions relate generally to vesiculin peptides and vesiculin peptide chains, and fragments, variants and derivatives thereof, related compositions and formulations and their preparation and use, nucleic acids encoding such vesiculin peptides and vesiculin peptide chains, and fragments, variants and derivatives thereof and related vectors and host cells, hybridomas and antibodies, and methods for the prevention and treatment of conditions, diseases and disorders that would be improved, eased, or lessened by the administration of a composition of the invention, including but not limited to glucose metabolism diseases.

10 Claims, 5 Drawing Sheets

(56) References Cited

OTHER PUBLICATIONS

Figure 1A:
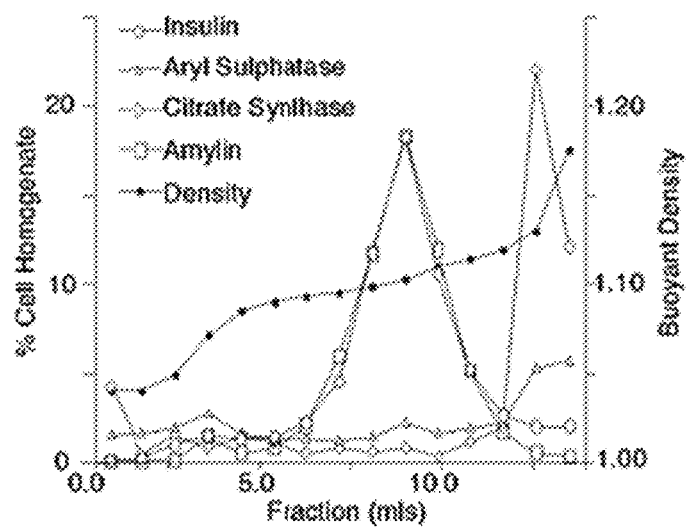

Haselbacher et al. (Apr. 1985) "Insulin-Like Growth Factor II (IGF II) in Human Brain: Regional Distribution of IGF II and of Higher Molecular Mass Forms," *Proc. Nat. Acad. Sci. USA* 82:2153-2157.
Hoekman et al. (1994) "Tumour-Induced Hypoglycaemia: A Case Report," *Ann. Oncol.* 5:277-281.
Hofmann et al. (1999) "The PROSITE Database, It's Status in 1999," *Nuc. Acids Res.* 27(1):215-219.
Huang, X. (1994) "On Global Sequence Alignment," *Comp. App. Bioscience.* 10:227-235.
Hudgins et al. (Apr. 1992) "The Identification of O-Glycosylated Precursors of Insulin-Like Growth Factor II," *J. Biol. Chem.* 267:8153.
Hutton et al. (1982) "Isolation and Characterisation of Insulin Secretory Granules from a Rat Islet Cell Tumor," *Diabetalogia* 2:365-373.
International Search Report, Corresponding to International Application No. PCT/NZ2006/000078, Mailed Aug. 4, 2006.
Janson et al. (Jan. 1985) "Nucleotide Sequences of cDNAs Encoding Precursors of Human Insulin-Like Growth Factor II (IGF-II) and an IGF-II Variant," *FEBS Lett.* 179(2):243-246.
Jansen et al. (Mar. 1990) "Effects of a Single Cleavage in Insulin-Like Growth Factors I and II on Binding to Receptors, Carrier Proteins and Antibodies," *Biochem. J.* 266(2):513-520.
Johnson et al. (1988) "Immunolocalization of Islet Amyloid Polypeptide (IAPP) in Pancreatic Beta Cells by Means of Peroxidase-Antiperoxidase (PAP) and Protein A-Gold Techniques," *Am. J. Pathol.* 130:1-8.
Kaytor et al. (2001) *J. Biol. Chem.* 276:36896-36901.
Ketcha-Kamoun et al. (2001) "Thymic Expression of Insulin-Related Genes in an Animal Model of Autoimmune Type 1 Diabetes," *Diabetes Metab. Res. Rev.* 17(2):146-152.
Kikuchi et al. (1991) "Sire-Specific Cleavage of Natural mRNA Sequences by Newly Designed Hairpin Cataytic RNA's," *Nuc. Acids Res.* 19(24):6751-6755.
Klein et al. (1985) "Retinopathy in Young-Onset Diabetic Patients," *Diabetes Care* 8(4):311-315.
Koenig et al. (1972) "Synaptic Vesicle Lipo Protein (Vesiculin): Relation to Neurophysin and Chromogranin," *Neurology* 22(4):415.
Koenig, H. (1974) "Soluble Acidic Lipoproteins (SALPS) of Storage Granules. Matrix Constituents Which May Bind Stored Molecules," *Adv. Cytopharm.* 2:273-301.
Kohler et al. (Aug. 1975) "Continuous Cultures of Fused Cells Secreting Antibody of Predefined Specificity," *Nature* 256:495-497.
Koizumi et al. (1998) *FEBS Lett.* 228:228-230.
Koizumi et al. (1989) "Design of RNA Enzymes Distinguishing a Single Base Mutation in RNA," *Nuc. Acids Res.* 17(17):7059-7069.
Luthi et al. (1992) "Mutants of Human Insulin-like Growth Factor 11 (IGF11)," *Eur. J. Biochem.* 205:483-490.
Maniatis et al. (1989) *Molecular Cloning—A Laboratory Manual*, Cold Spring Harbour Laboratories, Cold Spring Harbour, New York, pp. 16.2-16.80.
Marglin et al. (1970) "Chemical Synthesis of Peptides and Proteins," *Ann. Rev. Biochem.* 39:841-866.
Martin, T. (1989) "Cell Cracking: Permeabilizing Cells to Macromolecular Probes," *Methods Enzymol.* 68:225-233.
Merrifield, R.B. (1969) "The Synthesis of Biologically Active Peptides and Proteins," *JAMA* 210(7):1247-1254.
Merrifield (1963) "Solid Phase Synthesis: The Synthesis of a Tetrapaptide," *J. Am. Chem. Soc.* 85:2149-2154.
Needleman et al. (Mar. 1970) "A General Method Applicable to the Search for Similarities in the Amino Acid Sequence of Two Proteins," *J. Mol. Biol.* 48(3):443-453.
Nielsen et al. (Dec. 1991) "Sequence-Selective Recognition of DNA by Strand Displacement with a Thymine-Substituted Polyamide," *Science* 254(5037):1497-1500.
Notredame et al. (2000) "T-Coffee: A Novel Method for Fast and Accurate Multiple Sequence Alignment," *J. Mol. Biol.* 302:205-217.
Perdue et al. (1994) "Structural Determinants for the Binding of Insulin-Like Growth Factor-II to IIGF and Insulin Receptors and IGF Binding Proteins," *Int. Congr. Series* 1056:67-76.
Redd et al. (Apr. 1997) "A Complex Composed of Tup1 and Ssn6 Represses Transcription in Vitro," *J. Bio. Chem.* 272:11193-11197.
Rice et al. (Jun. 2000) "EMBOSS: The European Molecular Biology Open Software Suite," *Tends in Genet.* 16(6):276-277.
Rinderknecht et al. (Dec. 1976) "Amino-Terminal Sequences of Two Polypeptides from Human Serum with Nonsuppressible Insulin-Like and Cell-Growth-Promoting Activities: Evidence for Structural Homology with Insulin B Chain," *Proc. Nat. Acad. Sci. USA* 73(12):4379-4381.
Roth et al. (1991) "Mutants of Human Insulin-Like Growth Factor II: Expression and Characterization of Analogs with a Substitution of TYR27 and/or a Deletion of Residues 62-67," *Biochem. Biophys. Res. Commun.* 181:907-914.
Sakano et al. (Nov. 1991) "The Design, Expression, and Characterization of Human Insulin-Like Growth Factor II (IGF-II) Mutants Specific for Either the IGF-II/Cation-Independent Mannose 6-Phosphate Receptor of IGF-I Receptor," *J. Biol. Chem.* 266:20626-20635.
Sambrook et al. (1989) *Molecular Cloning: A Laboratory Manual*, $2^{nd}$ ed., Cold Spring Harbor Press.
Shapiro et al. (1990) "Tumor Hypoglycemia: Relationship to High Molecular Weight Insulin-Like Growth Factor-II," *J. Clin Invest.* 85:1672.
Soller et al. (1972) "Vesiculin: A Soluble Acidic Lipoprotein from Synaptic Vesicles Which May Bind Transmitter Amines," *Trans. Am. Neurol. Assoc.* 97:342-344.
Srere (1969) *Methods Enzymol.* 13:3-5.
Stadler et al.. (1978) "Identification of Vesiculin as a Glycosaminoglycan" Barin Research 153:408-413.
Tashiro et al. (1978) "Chemical Composition of Cholinergic Synaptic Vesicles from Torpedo marmormata Based on Improved Purification," Eur J Biochem 90:479-487.
Tatusova et al. (1999) "Blast 2 Sequences—A New Tool for Comparing Protein and Nucleotide Sequences," *FEMS Microbiol. Lett.* 174:247-250.
Tatusov et al. (Oct. 1997) "A Genomic Perspective on protein Families," *Science* 278:631-637.
Thompson et al. (1994) "CLUSTALW: Improving the Sensitivity of Progressive Multiple Sequence Alignment Through Sequence Weighting, Positions-Specific Gap Penalties and Weight Matrix Choice," *Nuc. Acids Res.* 22:4673-4680.
Ulmar et al. (1974) "Immunological Approach to the Characterization of Cholinergic Vesicular Protein," *J. Neurochem.* 22(3):451-454.
Walker et al. (1983) "Identification of a Proteoglycan Antigen Characteristic of Cholinergic Synaptic Vesicles," J Neurochem 41:209-216.
Weir et al. (Feb. 2001) "β-Cell Adaptation and Decompensation During the Progression of Diabetes," *Diabetes* 50(supp 1):S154-S159.
Whittaker et al. (1973) "The Structural and Chemical Properties of Synaptic Vesicles," In; *Proteins of the nervous System*, Schneider et al. eds., Raven Press: New York, N.Y. USA pp. 155-169.
Whittaker et al. (1973) "The Storage of Acetylcholine in Presynaptic Nerve Terminals," *Sci. Basis Med.* 17-31.
Whittaker et al. (1974) "Proteins of Cholinergic Synaptic Vesicles from the Electric Organ of *Torpedo*. Characterization of Low Molecular Weight Acidic Protein," *Brain Res.* 75(1):115-131.
Yang et al. (Feb. 1985) "Biosynthesis of Rat Insulin-Like Growth Factor II. II. Localization of Mature Rat Insulin-Like Growth Factor II (7484 Daltons) to the Amino Terminus of the Approximately 20-Kilodalton Biosynthetic Precursor by Radiosequence Analysis," *J. Biol. Chem.* 260:2578-2582.
Zarn et al. (1992) "Mutants of Human Insulin-like Growth Factor II (IGFII) with the Processing Sites of Proinsulin," *Eur. J. Biochm.* 210:665-669.
Zumstein et al. (May 1985) "Amino cid Sequence of a Variant Pro-Form of Insulin-Like Growth Factor II," *Proc. Nat. Acad. Sci. USA* 82:3169-3172.
Smith et al., (1989) "Structure and Activity Dependence of Recombinant Human-like Growth Factor II on Disulfide Bond Pairing," J. Bio. Chem. 264(16):9314-9321.

VESICULINS

CROSS-REFERENCE TO RELATED APPLICATIONS

This application claims the benefit of U.S. application Ser. No. 11/912,111, having a 371(c) date of Mar. 3, 2008; International Application No. PCT/NZ2006/000078, filed Apr. 20, 2006 and published in English on Oct. 26, 2006 as WO 2006/112737 A1, and U.S. Provisional Application No. 60/673,537, filed Apr. 20, 2005, all of which are incorporated by reference herein in their entirety.

FIELD OF THE INVENTION

The inventions relate generally to peptides and proteins and related compositions and formulations and their preparation and use, nucleic acids encoding such peptides and proteins and related vectors and host cells, and methods for the prevention and treatment of conditions, diseases and disorders that would be improved, eased, or lessened by the administration of a composition of the invention, including but not limited to glucose metabolism diseases and disorders and diseases and disorders and conditions treated or treatable with insulin and other hypoglycemic agents.

BACKGROUND OF THE INVENTION

The following includes information that may be useful in understanding the present inventions. It is not an admission that any of the information provided herein is prior art, or relevant, to the presently described or claimed inventions, or that any publication or document that is specifically or implicitly referenced is prior art.

Insulin-like growth factor II (IGF-II) is a polypeptide growth factor which stimulates the proliferation of a wide range of cell types. Originally reported from human serum, human IGF-II is a 7.5 kDa single-chain polypeptide containing 67 amino acid residues. Rinderknecht, E. and Humbel, R. *Proc. Natl. Acad. Sci.* USA 73:4379-4381 (1976). For a general review of IGF-II, see, e.g., Binoux M., *Diabete et Metabolisme*, "The IGF system in metabolism regulation" 21(5):330-7 (1995).

IGF-II may exist in various forms as a result of amino acid insertions (Jansen, M., et al., *FEBS Lett.* 179:243 (1985); Hampton, B., et al., *Journal of Biological Chemistry* 264: 19155-19160 (1989)), post-translational glycosylation (Hudgins, W., et al., *J. Biol. Chem.* 267:8153 (1992); Daughaday, et al., *Proc. Natl. Acad. Sci.* USA 90:5823-5827 (1993), differential processing of the COOH-terminal E-domain peptide (Hudgins, et al., *J. Biol. Chem.* 267:8153 (1992); Zumstein, P, et al., *Proc. Natl. Acad. Sci.* USA 82:3169-3172 (1985); Gowan, et al., *Endocrinol.* 121:449 (1987); Haselbacher and Humbel, *Endocrinol.* 110:1822 (1982); Haselbacher et al., *Proc. Natl. Acad. Sci.* USA 82:2153-2157 (1985); Daughaday, W., et al., *N. Engl. J. Med.* 319:1434 (1988); Shapiro et al., *J. Clin. Invest.* 85:1672 (1990); Hoekman, et al., *Annals in Oncology* 5:277 (1994)), and endoproteolysis (see Jansen, J., et al., *Biochem. J.* 266:513-520 (1990), reporting a double-chain molecule of IGF-II proposed to result from a naturally occurring single-point cleavage occurring between Ser29 and Arg30).

Altered IGF-II proteins have been reported, for example, [Leu27]-, [Glu27]-, and [Glu48]IGF-II (Burgisser, D., et al., *J. Biol. Chem.* 266:1029-1033 (1991)), and [Ser26]-, [Leu27]-, [Leu43]-, [Thr48, Ser49, Ile50]-, and [Arg54, Arg55]IGF-II (Sakano, K., et al., *J. Biol. Chem.* 266:20626-20635 (1991)). IGF-II deletion mutants have also been reported, for example, (7-67)- and (9-67)IGF-II (Luthi, C., et al., *Eur. J. Biochem.* 205:483-490 (1992)) and des(37-40)[Arg33]IGF-II (Zarn et al., *Eur. J. Biochem.* 210:665-669 (1992)). See also Roth, B., et al., "Mutants of human insulin-like growth factor II: expression and characterization of analogs with a substitution of TYR27 and/or a deletion of residues 62-67," *Biochem Biophys Res Commun.* 181:907-14 (1991).

Diabetes mellitus, characterized by hyperglycemia and altered β-cell function, is a common disorder affecting millions of Americans. According to statistics provided by the American Diabetes Association (ADA), there are 18.2 million people in the United States, or 6.3% of the population, who have diabetes. Direct medical and indirect expenditures attributable to diabetes in 2002 were estimated at $132 billion.

Type 1 and type 2 diabetes are both diseases of the pancreas characterized by hyperglycemia. In type 1 diabetes the pancreatic islet β-cells, which secrete both insulin and amylin, peptide hormones that exert profound effects on glucose metabolism, are destroyed. In type 2 diabetes these cells progressively lose function, and often fail in the late stages of the disease. As one would expect given the severity of diabetes, and difficulties associated with it, the islet β-cells play a major role in physiology.

While therapeutic regimens exist to replace insulin and amylin function, diabetic individuals remain prone to complications which are a major threat to both the quality and the quantity of life. Many patients with diabetes die early, often as a result of cardiovascular or renal complications, preceded by many years of crippling and debilitating disease beforehand. It is estimated that diabetic individuals have a 25-fold increase in the risk of blindness, a 20-fold increase in the risk of renal failure, a 15- to 40-fold increase in the risk of amputation as a result of gangrene, and a 2- to 6-fold increased risk of coronary heart disease and ischemic brain damage. See, Klein R., et al., *Diabetes Care* 8:311-5 (1985). The ADA reports that two out of three people with diabetes die from heart disease and stroke, that diabetes is the leading cause of new cases of blindness in people ages 20-74 (with 12,000 to 24,000 people losing their sight because of diabetes), that diabetes is the leading cause of end-stage renal disease (kidney failure), accounting for about 43 percent of new cases (with approximately 41,046 people with diabetes initiating treatment for end stage renal disease and 129,183 undergoing dialysis or kidney transplantation in the year 2000), that more than 60 percent of nontraumatic lower-limb amputations in the U.S. occur among people with diabetes (with more than 82,000 amputations are performed among people with diabetes), that people with diabetes are two to four times more likely to suffer strokes (and once having had a stroke, are two to four times as likely to have a recurrence), that deaths from heart disease in women with diabetes have increased 23 percent over the past 30 years (compared to a 27 percent decrease in women without diabetes), and that deaths from heart disease in men with diabetes have decreased by only 13 percent (compared to a 36 percent decrease in men without diabetes).

Type 1 diabetes is characterized by an early loss of endocrine function in the pancreas due to autoimmune destruction of the pancreatic islet β-cells, resulting in hypoinsulinemia, hypoamylinemia, and hyperglycemia. Type 2 diabetes is a polygenic and heterogeneous disease resulting from an interaction between genetic factors and environmental influences. See, e.g., Kecha-Kamoun et al., *Diabetes Metab Res Rev* 17:146-152 (2001).

Although type 2 diabetes is initially characterized by hyperinsulinemia, peripheral insulin resistance and resulting hyperglycemia characterize type 2 diabetes. β-cells often compensate for this insulin resistance with both an increase in insulin secretory capacity and β-cell mass. Levels of insulin eventually decrease as a result of the loss of β-cell function and eventual β-cell failure. Thus, there is a progression from normal glucose tolerance, to impaired glucose tolerance, to type 2 diabetes, and to late stage type 2 diabetes, which is associated with altered β-cell function, β-cell loss and, eventually, a decline in insulin secretion. See, e.g., Dickson et al., *J. Biol. Chem.* 276:21110-21120 (2001). In other words, hyperglycemia worsens as β-cells fail to sustain levels of insulin output sufficient to overcome increasing resistance to insulin. Kaytor, et al., *J Biol Chem.* 16:16 (2001). Eventual β-cell failure is primarily a failure in function but later proceeds to β-cell loss such as that seen in type 1 diabetes. One of the most striking functional β-cell defects is a loss of acute glucose-induced insulin secretion (GIIS). β-cells initially adapt to increased demand for insulin but then decompensate as type 2 diabetes worsens. One hypothesis is that β-cells can become de-differentiated, leading to a loss of specialized functions, such as GIIS. Weir et al., *Diabetes,* 50 Supplement 1, S154-S159 (2001).

It is understood that integrated networks of signaling events act in concert to control β-cell mass adaptation to insulin demand, and there is some evidence to suggest that increased β-cell growth might in some part be due to a circulating growth factor. See, e.g., Flier et al. (2001) *Proc. Nat. Acad. Sci.* USA, 98:7475-7480, which reported that transplantation of normal islets into the pancreas or kidney capsule of insulin resistant mice led to a marked increase in β-cell mass.

Despite decades of research into diabetes and its causes, despite enormous research on β-cells themselves and the proteins they produce, and despite the existence and use of therapies for the treatment of people with type 1 and type 2 diabetes, serious problems remain.

The identification of other relevant proteins relating to diabetes and the pancreas, for example, β-cell proteins, would be of great benefit in the continuing effort to further improve the lives of people with diabetes including, for example, proteins that increase β-cell mass and address issues relating to hyperglycemia and the long-term complications of diabetes and the loss of circulating proteins as a result of β-cell destruction.

A new β-cell peptide hormone has been discovered and is described and claimed herein. The peptide has bioactivity including increasing glucose uptake.

SUMMARY OF THE INVENTION

The inventions described and claimed herein have many attributes, aspects, and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

The inventions described and claimed herein relate to the discovery of a previously unknown peptide, termed vesiculin. The peptide is present in pancreatic β-cell secretory granules, including human β-cell secretory granules.

In a first aspect isolated vesiculins are provided. Also provided are vesiculin nucleic acid sequences. Vesiculins and vesiculin polynucleotides may be recombinant, isolated, pure or purified, or substantially pure.

In another aspect vesiculin A chain polypeptides and polynucleotides are provided, for example, human vesiculin A chain polypeptides and polynucleotides. Also provided are A chain fragments.

In yet another aspect vesiculin B chain polypeptides and polynucleotides are provided, for example, human vesiculin B chain polypeptides and polynucleotides. Also provided are B chain fragments.

Vesiculin A and B chain polypeptides and fragments, and polynucleotides coding therefor, may be recombinant, isolated, pure or purified, or substantially pure.

In still another aspect, vesiculin variants, vesiculin derivatives, and active fragments of vesiculin are provided.

As used herein, "vesiculin" refers to a polypeptide comprising a two chain peptide having 62 or 63 amino acids. The human sequence may be represented as follows:

(SEQ ID NO: 1)
A chain: Gly Ile Val Glu Glu $Cys_3$ $Cys_4$ Phe Arg Ser
$Cys_5$ Asp Leu Ala Leu Leu Glu Thr Tyr $Cys_6$ Ala Thr
Pro Ala Lys Ser Glu (SEQ ID NO: 56)
B chain: $Ala_1$ Tyr Arg Pro Ser Glu Thr Leu $Cys_1$ Gly
Gly Glu Leu Val Asp Thr Leu Gln Phe Val $Cys_2$ Gly
Asp Arg Gly Phe Tyr Phe Ser Arg Pro Ala Ser Arg
Val Ser wherein $Ala_1$ is either present or absent.

Vesiculin variants are also provided and include, for example:

(SEQ ID NO: 2)
A chain: Gly Ile Val Glu Glu $Cys_3$ $Cys_4$ Phe Arg Ser
$Cys_5$ Asp Leu Ala Leu Leu Glu Thr Tyr $Cys_6$ Ala $R_7$
Pro Ala Lys Ser Glu (SEQ ID NO: 57)
B chain: $Ala_1$ Tyr $R_1$ Pro $R_2$ Glu Thr Leu $Cys_1$ Gly
Gly Glu Leu Val Asp Thr Leu Gln Phe Val $Cys_2$ $R_3$
Asp Arg Gly Phe Tyr Phe Ser Arg Pro $R_4$ Ser Arg
$R_5$ $R_6$ wherein $Ala_1$ is either present or absent; $R_1$ is Gly or Arg; $R_2$ is Gly or Ser; $R_3$ is Gly or Ser; $R_4$ is Ser or Ala; $R_5$ is Ile or Val or Ala either; $R_6$ is Asn or Ser; and $R_7$ is Thr or Ala. In yet another embodiment, $Ala_1$ is either present or absent; $R_1$ is Gly or Arg, or a conservative variant of either; $R_2$ is Gly or Ser, or a conservative variant of either; $R_3$ is Gly or Ser, or a conservative variant of either; $R_4$ is Ser or Ala, or a conservative variant of either; $R_5$ is Ile or Val or Ala, or a conservative variant of either; $R_6$ is Asn or Ser, or a conservative variant of either; and $R_7$ is Thr or Ala, or a conservative variant of either.

Additional vesiculin variants include, for example:

(SEQ ID NO: 3)
A chain: Gly Ile Val Glu Glu $Cys_3$ $Cys_4$ Phe Arg Ser $Cys_5$ Asp Leu $R_1$ $R_2$ Leu Glu $R_3$ Tyr $Cys_6$ Ala $R_4$ $R_5$ $R_6$ $R_7$ $R_8$ $R_9$ (SEQ ID NO: 58)
B chain: $R_{10}$ $R_{11}$ $R_{12}$ $R_{13}$ $R_{14}$ Glu Thr Leu $Cys_1$ Gly Gly Glu Leu Val Asp $R_{15}$ Leu Gln Phe $R_{16}$ $Cys_2$ $R_{17}$ $R_{18}$ Arg Gly Phe Tyr Phe $R_{19}$ $R_{20}$ $R_{21}$ $R_{22}$ $R_{23}$ $R_{24}$ $R_{25}$ $R_{26}$ $R_{27}$ $R_{28}$ $R_{29}$ wherein $R_1$ is Ala, Asn or Leu; $R_2$ is Leu or Ile; $R_3$ is Thr or Gln; $R_4$ is Thr, Ala, Lys, or Val; $R_5$ is Pro or Ser; $R_6$ is Ala, Val, or Pro; $R_7$ is Lys or Glu, $R_8$ is Ser or Ala, $R_9$ is Glu or Ala, $R_{10}$ is absent or is Ala, Glu, or Asp, $R_{11}$ is Tyr, Ala, or Val, $R_{12}$ is Arg, Gly, or Ala, $R_{13}$ is Pro, Thr, Ser, or Leu, $R_{14}$ is Ser, Gly, Ala, or Glu, $R_{15}$ is Thr or Ala, $R_{16}$ is Val or Ile, $R_{17}$ is Gly, Ser, Glu, or Ala, $R_{18}$ is Asp or Glu, $R_{19}$ is Ser or Val, $R_{20}$ is Arg, Leu, or Ser, $R_{21}$ is Pro or Lys, $R_{22}$ is Ala, Ser, Gly, Val, or Thr, $R_{23}$ is Ser, Gly, or Val, $R_{24}$ is Arg, Pro or Gly, $R_{25}$ is Ala, Arg, Val, Ile, Leu, Asn, Ser, or Gly, $R_{26}$ is Ser, Asn, or Arg, $R_{27}$ is absent or is Arg, Ser, Asn, $R_{28}$ is absent or is Val, $R_{29}$ is absent or is Ser. In certain embodiments, $R_1$-$R_{29}$ include conservative amino acid variants for the amino acids listed above. Thus, $R_1$ is Ala, Asn, Leu, or a conservative variant of either, $R_2$ is Leu, Ile, or a conservative variant of either, $R_3$ is Thr, Gln, or a conservative variant of either, $R_4$ is Thr, Ala, Lys, Val, or a conservative variant of either, $R_5$ is Pro, Ser, or a conservative variant of either, $R_6$ is Ala, Val, Pro, or a conservative variant thereof, $R_7$ is Lys, Glu, or a conservative variant of either, $R_8$ is Ser, Ala, or a conservative variant of either, $R_9$ is Glu, Ala, or a conservative variant of either, $R_{10}$ is absent or is Ala, Glu, Asp, or a conservative variant thereof, $R_{11}$ is Tyr, Ala, Val, or a conservative variant of either, $R_{12}$ is Arg, Gly, Ala, or a conservative variant thereof, $R_{13}$ is Pro, Thr, Ser, Leu, or a conservative variant thereof, $R_{14}$ is Ser, Gly, Ala, Glu, or a conservative variant thereof, $R_{15}$ is Thr, Tyr, Ala, or a conservative variant thereof, $R_{16}$ is Val, Ile, or a conservative variant thereof, $R_{17}$ is Gly, Ser, Glu, Ala, or a conservative variant thereof, $R_{18}$ is Asp, Glu, or a conservative variant of either, $R_{19}$ is Ser, Val, or a conservative variant of either, $R_{20}$ is Arg, Leu, Ser, or a conservative variant thereof, $R_{21}$ is Pro, Lys, or a conservative variant of either, $R_{22}$ is Ala, Ser, Gly, Val, Thr, or a conservative variant thereof, $R_{23}$ is Ser, Gly, Val, or a conservative variant thereof, $R_{24}$ is Arg, Pro, Gly, or a conservative variant thereof, $R_{25}$ is Ala, Arg, Val, Ile, Leu, Asn, Ser, Gly, or a conservative variant thereof, $R_{26}$ is Ser, Asn, Arg, or a conservative variant thereof, $R_{27}$ is absent or is Arg, Ser, Asn, or a conservative variant thereof, $R_{28}$ is absent or is Val, or a conservative variant thereof, $R_{29}$ is absent or is Ser, or a conservative variant thereof.

In one embodiment the vesiculin comprises A and B chains joined by at least one inter-chain disulfide bond. For example, the vesiculin may include disulfide bonds formed between any one of $Cys_1$, $Cys_2$, $Cys_3$, $Cys_4$, $Cys_5$ and $Cys_6$ residues.

In another embodiment the vesiculin comprises A and B chains joined by two inter-chain disulfide bonds. For example, in one embodiment the vesiculin includes disulfide bonds formed between residues $Cys_1$ and $Cys_4$, and $Cys_2$ and $Cys_6$.

In another embodiment the vesiculin comprises an intra-chain disulfide bond in chain A between residues $Cys_3$ and $Cys_5$.

In another embodiment the vesiculin comprises A and B chains joined by one or more inter-chain disulfide bonds and an A-chain intra-chain disulfide bond. For example, in one embodiment the vesiculin includes disulfide bonds formed between residues $Cys_1$ and $Cys_4$, and $Cys_2$ and $Cys_6$, and $Cys_3$ and $Cys_5$.

Also provided are vesiculin variants, derivatives or active fragments having a vesiculin B chain from any species (for example, human, rat, mouse, etc.) and a vesiculin A chain having the sequence GIVEECCFRSCDLALLETYCATPAKSE. (SEQ ID NO:4).

Active vesiculin fragments include those with an A chain having from one to six C-terminal amino acid residue deletions (or corresponding nucleotide deletions in the case of polynucleotides encoding active fragments). Human A chain fragments included in active vesiculin fragments include, for example, the following polypeptides (and corresponding polynucleotides):

(SEQ ID NO: 5)
GIVEECCFRSCDLALLETYCATPAKS;

(SEQ ID NO: 6)
GIVEECCFRSCDLALLETYCATPAK;

(SEQ ID NO: 7)
GIVEECCFRSCDLALLETYCATPA;

(SEQ ID NO: 8)
GIVEECCFRSCDLALLETYCATP;

(SEQ ID NO: 9)
GIVEECCFRSCDLALLETYCAT;
and, (SEQ ID NO: 10)
GIVEECCFRSCDLALLETYCA.

Corresponding A chain fragments from other species, and vesiculins from other species incorporating those fragments, are also provided by the invention.

Active vesiculin fragments include those with a B chain having from one to four C-terminal amino acid residue deletions (or corresponding nucleotide deletions in the case of polynucleotides encoding active fragments). Human B chain fragments included in active vesiculin fragments include, for example, the following polypeptides (and corresponding polynucleotides):

(SEQ ID NO: 11)
AYRPSETLCGGELVDTLQFVCGDRGFYFSRPASRV;

(SEQ ID NO: 12)
AYRPSETLCGGELVDTLQFVCGDRGFYFSRPASR;

(SEQ ID NO: 13)
AYRPSETLCGGELVDTLQFVCGDRGFYFSRPAS;
and, (SEQ ID NO: 14)
AYRPSETLCGGELVDTLQFVCGDRGFYFSRPA.

Corresponding B chain fragments from other species, and vesiculins from other species incorporating those fragments, are also provided by the invention.

Active vesiculin fragments also include those having an A chains with from one to six C-terminal amino acid residue deletions and a B chain with from one to four C-terminal amino acid residue deletions (and corresponding polynucleotides). These include active human vesiculin fragments including an A chain fragment and a B chain fragment, as well as active fragments of other vesiculin species including an A chain fragment and a B chain fragment. They also include vesiculin fragments having an A chain fragment from one species combined with a B chain fragment from another species.

Active vesiculin fragments also include those having an A chain with from one to six C-terminal amino acid residue deletions and a full length B chain (and corresponding polynucleotides). These include active human vesiculin fragments with an A chain fragment and a full length B chain, as well as similar molecules from other vesiculin species. They also include vesiculin fragments having an A chain fragment from one species combined with a full length B chain from another species.

Active vesiculin fragments also include those having a full length A chain and a B chain with from one to four C-terminal amino acid residue deletions (and corresponding polynucleotides). These include active human vesiculin fragments with a full length A chain and a B chain fragment, as well similar molecules from other vesiculin species. They also include vesiculin fragments having a full length A chain from one species combined with a B chain fragment from another species.

Other embodiments include vesiculin variants having an amino acid sequence that is at least about 60% identical to a vesiculin, for example, a human vesiculin. In other embodiments, a vesiculin variant may contain an amino acid sequence that is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 98.5%, or at least about 99% identical to a vesiculin, for example, a human vesiculin.

In one embodiment, the vesiculin polypeptide or variant or derivative or active fragment thereof has a serine at position 33 of the B chain. In other embodiments, the vesiculin polypeptide or variant or derivative or active fragment thereof has an amino acid other than arginine at position 33 of the B chain. In another embodiment, the vesiculin polypeptide or variant or derivative or active fragment thereof has a serine at position 36 of the B chain. In other embodiments, the vesiculin polypeptide or variant or derivative or active fragment thereof has an amino acid other than lysine at position 36 of the B chain. In other embodiments, the vesiculin polypeptide or variant or derivative or active fragment thereof has serine residues at positions 33 and 36 of the B chain. In other embodiments, the vesiculin polypeptide or variant or derivative or active fragment thereof has an amino acid other than arginine at position 33 of the B chain, and additionally has an amino acid other than lysine at position 36 of the B chain. (The position numbering corresponds to that of human vesiculin.)

In another aspect, the invention relates to a method of modulating blood glucose levels in a subject. The method comprises administering an effective amount of one or more of a vesiculin, or a vesiculin variant, derivative, or active fragment, or a salt of any of them, to a subject in need thereof.

The invention includes methods for treating and/or preventing, in whole or in part, various diseases, disorders, and conditions, including for example, impaired glucose tolerance; impaired fasting glucose; prediabetes; diabetes and/or its complications, including type 1 and type 2 diabetes and their complications; insulin resistance; Syndrome X; obesity and other weight related disorders; fatty liver disease, including non alcoholic and/or alcoholic fatty liver disease; glucose metabolism diseases and disorders; diseases, disorders or conditions that are treated or treatable with insulin; diseases, disorders or conditions that are treated or treatable with a hypoglycemic agent; diseases, disorders, and conditions characterized at least in part by hyperglycemia; diseases, disorders, and conditions characterized at least in part by hypoinsulinemia and/or diseases, disorders, and conditions characterized at least in part by hyperinsulinemia.

The invention includes methods for treating a subject having or suspected of having or predisposed to, or at risk for, for example, any diseases, disorders and/or conditions characterized in whole or in part by hyperglycemia, insulin resistance, impaired glucose tolerance, and/or impaired fasting glucose, comprising administering a composition comprising a vesiculin, a vesiculin A chain, a vesiculin B chain, a vesiculin variant, a vesiculin derivative and/or a vesiculin fragment or a salt thereof. Such diseases, disorders and/or conditions include but are not limited to those described or referenced herein. Such compounds may be administered in amounts, for example, that are effective to (1) lower serum glucose, (2) lower blood glucose, (3) lower urine glucose, (4) lower fructosamine, (5) lower glycosylated hemoglobin ($HbA_{1c}$) levels, (6) lower postprandial glycemia, (7) ameliorate impaired glucose tolerance, (8) ameliorate impaired fasting glucose, and/or (9) lower the rate and/or severity of hypoglycemic events, including severe hypoglycemic events. Such compositions include, for example, formulations for delivery by injection, transdermal patch, inhalation, and other non-oral delivery methods.

The invention includes methods for regulating glycemia in a subject having or suspected of having or predisposed to diseases, disorders and/or conditions characterized in whole or in part, for example, by hyperglycemia, insulin resistance, impaired glucose tolerance, and/or impaired fasting glucose, comprising administering a composition comprising a vesiculin, a vesiculin A chain, a vesiculin B chain, a vesiculin variant, a vesiculin derivative and/or a vesiculin fragment or a salt thereof. Such diseases, disorders and/or conditions include but are not limited to those described or referenced herein. Such compounds may be administered in amounts, for example, that are effective to (1) lower serum glucose, (2) lower blood glucose, (3) lower urine glucose, (4) lower fructosamine, (5) lower glycosylated hemoglobin ($HbA_{1c}$) levels, (6) lower postprandial glycemia, (7) ameliorate impaired glucose tolerance, (8) ameliorate impaired fasting glucose, and/or (9) lower the rate and/or severity of hypoglycemic events, including severe hypoglycemic events. Such compositions include, for example, formulations for delivery by injection, transdermal patch, inhalation, and other non-oral delivery methods.

In another aspect, the invention relates to a use of one or more of a vesiculin, or a vesiculin variant, derivative, or active fragment, or a salt of any of them, in the preparation of a medicament, including medicaments for modulating blood glucose levels in a subject.

In another aspect, the invention relates to a method of modulating glucose incorporation into glycogen in a subject. The method comprises administering an effective amount of one or more of a vesiculin, or a vesiculin variant, derivative, or active fragment thereof, or a salt of any of them, to a subject in need thereof.

In another aspect the invention is directed to the use of an effective amount of one or more of a vesiculin, or a vesiculin variant, derivative, or active fragment, or a salt of any of them, in the manufacture, with or without other pharmaceutically acceptable materials (such as, for example, excipients, diluents or the like, and/or within a dosage unit defining vessel), of a dosage unit effective for use in a method of the invention or for any of the purposes herein described or provided.

The invention also includes vesiculin, vesiculin variants, derivatives or active fragments produced by, for example, recombinant expression and protein synthesis techniques, followed by isolation and/or purification, as disclosed herein or by methods known in the art. Polynucleotides encoding vesiculins and vesiculin variants, derivatives, and active fragments are also provided.

In various embodiments, vesiculin, vesiculin A chain, and vesiculin B chain polynucleotides, and vesiculin variants and derivatives, vesiculin A chain variants and derivatives, and vesiculin B chain variants and derivatives are at least about 60%, or at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5%, identical to the polynucleotide that encodes the polypeptide of SEQ ID NO:1, or SEQ ID NO:56, or the polynucleotide that encodes any vesiculin polypeptide recited herein.

Also provided are vectors, including cloning vectors and expression vectors, which comprise a polynucleotide that encodes and is capable of expressing a vesiculin, a vesiculin A chain, a vesiculin B chain, or a vesiculin, vesiculin A chain, or vesiculin B chain variant or derivative, or an active fragment thereof. Also provided are host cells comprising one or more of said vectors, as well as recombinant host cells comprising a heterologous polynucleotide encoding a vesiculin, a vesiculin A chain, a vesiculin B chain, or a vesiculin, vesiculin A chain, and/or vesiculin B chain variant or derivative, or active fragment thereof.

The invention further includes a pharmaceutical composition which comprises a vesiculin, a vesiculin A chain, a vesiculin B chain, or a vesiculin, vesiculin A chain, or vesiculin B chain variant or derivative, or an active fragment thereof, or salts or derivatives of the above.

The invention includes methods for generating antibodies reactive against vesiculin comprising administering vesiculin, or a variant, derivative or fragment thereof as an immunogen to an animal, and harvesting the antibodies from said animal.

The invention includes antibodies which bind a vesiculin, a vesiculin A chain, and/or a vesiculin B chain, and antibodies which bind a vesiculin variant, a vesiculin A chain variant, and/or a vesiculin B chain variant, or a vesiculin, vesiculin A chain, or vesiculin B chain derivative or fragment, assays which employ such antibodies, including monoclonal antibody-based sandwich assays and RIAs, and assay kits which contain such antibodies.

The vesiculins, vesiculin A and B chains, and variants and derivatives and fragments thereof for use in the methods of the invention may be formulated in a manner suitable for administration to a subject, for example, a human. Administration is preferably, for example, parenteral via routes such as subcutaneous (s.c.), intradermal (i.d.), intravenous (i.v.), intraperitoneal (i.p.) or transdermal, although other delivery form are envisioned, including oral, nasal, and pulmonary, for example.

These and other features, objects, and advantages of the inventions, which are not limited to or by the information in this Brief Summary, will be apparent from the further description provided herein, including the drawings and the claims.

BRIEF DESCRIPTION OF THE DRAWINGS

FIG. 1A shows assays for marker proteins indicating the localization of organelles from βTC6-F7 cells within a continuous OptiPrep gradient, including granule core (insulin), granule matrix (amylin), lysosomes (aryl sulphatase), mitochondria (citrate synthase).

FIG. 1B shows the purification of granule proteins by Reverse phase-high performance liquid chromatography (RP-HPLC).

FIG. 2A shows RP-HPLC purification of the hatched peak from FIG. 1B. Further RP-HPLC purification yielded 2 major peaks, with the second peak analyzed by Matrix assisted laser desorption/ionization-time of flight (MALDI-TOF) mass spectrometry and determined to have a molecular weight indicating a processed form of IGF-II (see Table 1). This peak was collected and subjected to reduction and alkylation.

FIG. 2B shows an RP-HPLC profile of reduced and alkylated vesiculin. These peaks were collected and subjected to proteolytic digestion by protease Asp-N.

FIG. 2C shows an RP-HPLC profile from Asp-N digest of purified vesiculin A-chain. Peaks marked A1-A3 were analyzed by MALDI-TOF mass spectrometry. Peak A2 yielded a molecular weight similar to $G_{41}$-$C_{51}$ (see Table 1). Peaks A1-A3 were also subjected to $NH_2$-terminal sequencing, the results of which are provided in Table 2.

FIG. 2D shows an RP-HPLC profile following an Asp-N digest of purified vesiculin B-chain. Peaks marked B1-B3 were analyzed by MALDI-TOF mass spectrometry. Peaks B1 and B3 yielded molecular weights similar to $D_{23}$-$N_{36}$ and $A_1$-$V_{14}$, respectively (see Table 1). Peaks B1-B3 were also subjected to $NH_2$-terminal sequencing, the results of which are provided in Table 2.

FIG. 3A shows the primary structure of IGF-II (a single-chain polypeptide consisting of 67 amino acids, IGF-II domains B, C, A, D, E).

FIG. 3B shows the polypeptide structure of IGF-II and a vesiculin.

FIG. 4 shows the effects of various concentrations of vesiculin on glucose incorporation into muscle glycogen in the rat soleus muscle assay. Dose response curves for (□) mouse-vesiculin, (●) mouse insulin II, and (○) human IGF-II.

DETAILED DESCRIPTION OF THE INVENTION

This invention relates in one aspect to one or more of a vesiculin, a vesiculin A chain, a vesiculin B chain, a vesiculin variant, vesiculin A chain and vesiculin B chain variants, and vesiculin, vesiculin A chain and vesiculin B chain derivatives, and salts thereof.

Amino acid sequences for mouse, human and rat vesiculin include the following:

```
AYGPGETLCGGELVDTLQFVCSDRGFYFSRPSSRAN (SEQ ID NO: 15)
GIVEECCFRSCDLALLETYCATPAKSE          (SEQ ID NO: 59)

AYRPSETLCGGELVDTLQFVCGDRGFYFSRPASRVS (SEQ ID NO: 16)
GIVEECCFRSCDLALLETYCATPAKSE          (SEQ ID NO: 60)
```

-continued
```
AYRPSETLCGGELVDTLQFVCSDRGFYFSRPSSRAN (SEQ ID NO: 17)
    |                \
    GIVEECCFRSCDLALLETYCATPAKSE        (SEQ ID NO: 61)
    └──┘
```

Vesiculin can be encoded by polynucleotides having the following nucleotide sequences:

```
Mouse:
                                                     (SEQ ID NO: 18)
gcttacggcc ccggagagac tctgtgcgga ggggagcttg ttgacacgct tcagtttgtc tgttcggacc gcggcttcta cttcagcagg ccttcaagcc gtgccaacgg catcgtggaa gagtgctgct tccgcagctg cgacctggcc ctcctggaga catactgtgc cacccccgcc aagtccgag Active vesiculin fragments include those with an A chain having from one to six C-terminal amino acid residue deletions (or corresponding nucleotide deletions in the case of polynucleotides encoding active fragments). Human A chain fragments included in active vesiculin fragments include, for example, the following polypeptides (and corresponding polynucleotides):

```
                                         (SEQ ID NO: 5)
GIVEECCFRSCDLALLETYCATPAKS;

(SEQ ID NO: 6)
GIVEECCFRSCDLALLETYCATPAK;

(SEQ ID NO: 7)
GIVEECCFRSCDLALLETYCATPA;

(SEQ ID NO: 8)
GIVEECCFRSCDLALLETYCATP;

(SEQ ID NO: 9)
GIVEECCFRSCDLALLETYCAT;
and, (SEQ ID NO: 10)
GIVEECCFRSCDLALLETYCA.
```

Corresponding A chain fragments from other species, and vesiculins from other species incorporating those fragments, are also provided by the invention.

Active vesiculin fragments include those with a B chain having from one to four C-terminal amino acid residue deletions (or corresponding nucleotide deletions in the case of polynucleotides encoding active fragments). Human B chain fragments included in active vesiculin fragments include, for example, the following polypeptides (and corresponding polynucleotides):

```
                                        (SEQ ID NO: 11)
AYRPSETLCGGELVDTLQFVCGDRGFYFSRPASRV;

(SEQ ID NO: 12)
AYRPSETLCGGELVDTLQFVCGDRGFYFSRPASR;

(SEQ ID NO: 13)
AYRPSETLCGGELVDTLQFVCGDRGFYFSRPAS;
and, (SEQ ID NO: 14)
AYRPSETLCGGELVDTLQFVCGDRGFYFSRPA.
```

Corresponding B chain fragments from other species, and vesiculins from other species incorporating those fragments, are also provided by the invention.

Active vesiculin fragments also include those having an A chain with from one to six C-terminal amino acid residue deletions and a B chain with from one to four C-terminal amino acid residue deletions (and corresponding polynucleotides). These include active human vesiculin fragments including an A chain fragment and a B chain fragment, as well as active fragments of other vesiculin species including an A chain fragment and a B chain fragment. They also include vesiculin fragments having an A chain fragment from one species combined with a B chain fragment from another species.

Active vesiculin fragments also include those having an A chain with from one to six C-terminal amino acid residue deletions and a full length B chain (and corresponding polynucleotides). These include active human vesiculin fragments with an A chain fragment and a full length B chain, as well as similar molecules from other vesiculin species. They also include vesiculin fragments having an A chain fragment from one species combined with a full length B chain from another species.

Active vesiculin fragments also include those having a full length A chain and a B chain with from one to four C-terminal amino acid residue deletions (and corresponding polynucleotides). These include active human vesiculin fragments with a full length A chain and a B chain fragment, as well similar molecules from other vesiculin species. They also include vesiculin fragments having a full length A chain from one species combined with a B chain fragment from another species.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); The Immunoassay Handbook (David Wild, ed., Stockton Press NY, 1994); Antibodies: A Laboratory Manual (Harlow et al., eds., 1987); and Methods of Immunological Analysis (R. Masseyeff, W. H. Albert, and N. A. Staines, eds., Weinheim: VCH Verlags gesellschaft mbH, 1993).

An "antibody" (interchangeably used in plural form) is an immunoglobulin molecule capable of binding to a target, including polynucleotides and polypeptides, through at least one antigen recognition site, located in the variable region of the immunoglobulin molecule. As used herein, the term encompasses not only intact antibodies, but also fragments of an antibody (such as Fab, Fab', F(ab')$_2$, Fv), single chain (ScFv), mutants thereof, fusion proteins comprising an antibody portion, humanized antibodies, and any other modified configuration of the immunoglobulin molecule that comprises an antigen recognition site of the desired specificity. Preferred antibodies do not cross-react, or undesirably cross-react, with IGF-II.

A "conservative amino acid substitution" is one in which an amino acid residue is replaced with another residue having a chemically similar or derivatized side chain. Families of amino acid residues having similar side chains, for example, have been defined in the art. These families include, for example, amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid analogs (e.g., phosphorylated amino acids) are also contemplated in the present invention, as are peptides substituted with non-naturally occurring amino acids, including but not limited to D-amino acids, β amino acids, and γ amino acids.

As used herein "purified" does not require absolute purity; rather, it is intended as a relative term where the subject protein or other substance is more pure than in its natural environment within a cell or other environment, such as a manufacturing environment. In practice the material has typically, for example, been subjected to fractionation to remove various other components, and the resultant material has substantially retained its desired biological activity or activities. The term "substantially purified" refers to peptides that are at least about 60% free, preferably at least about 75% free, and most preferably at least about 90% free, at least about 95% free, at least about 98% free, or more, from other components with which they may be associated naturally or during manufacture.

Also within the scope of this invention is a pharmaceutical composition that contains an effective amount of one or more of a vesiculin, a vesiculin A chain, a vesiculin B chain, a vesiculin variant, vesiculin A chain and vesiculin B chain variants, and vesiculin, vesiculin A chain and vesiculin B chain derivatives, and active fragments thereof, and salts of any of them, and a pharmaceutically acceptable carrier.

The term "pharmaceutically acceptable carrier" refers to a carrier (adjuvant or vehicle) that may be administered to a subject together with one or more of a vesiculin, a vesiculin A chain, a vesiculin B chain, a vesiculin variant, vesiculin A chain and vesiculin B chain variants, and vesiculin, vesiculin A chain and vesiculin B chain derivatives, and salts of any of them.

Pharmaceutically acceptable carriers that may be used in the pharmaceutical compositions described above include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents, which are commonly used in the formulation of pharmaceutically acceptable dosage forms such as emulsions and or suspensions.

An "effective amount" is an amount sufficient to effect beneficial or desired results including clinical results. An effective amount can be administered in one or more administrations by various routes of administration.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

As used herein, "treatment" is an approach for obtaining beneficial or desired results including clinical results although the term also encompasses prophylactic and/or therapeutic treatments.

The terms "polypeptide" and "peptide" and the like are used interchangeably herein to refer to any polymer of amino acid residues of any length. The polymer can be linear or non-linear (e.g., branched), it can comprise modified amino acids or amino acid analogs, and it can be interrupted by chemical moieties other than amino acids. The terms also encompass an amino acid polymer that has been modified naturally or by intervention; for example, by disulfide bond formation, glycosylation, lipidation, acetylation, phosphorylation, or any other manipulation or modification, such as conjugation with a labeling or bioactive component.

An "active fragment" of a polypeptide is a subsequence of the polypeptide that performs a function that is required for the biological activity and/or provides a three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing any one or more of the methods herein described, particularly with reference to modulating glucose.

The terms "polynucleotide" and "nucleic acid" are used interchangeably herein and refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. It is understood that the double stranded polynucleotide sequences described herein also include the modifications described herein. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH2) or a mixed phosphoramidate-phosphodiester oligomer. A phosphorothioate linkage can be used in place of a phosphodiester linkage. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

A "fragment" of a polynucleotide sequence provided herein is a subsequence of contiguous nucleotides that is capable of specific hybridization to a target of interest, for example, a sequence that is at least about 15 nucleotides in length. The polynucleotide fragment of the invention comprise about 15 nucleotides, preferably at least about 20 nucleotides, more preferably at least about 30 nucleotides, more preferably at least about 40 nucleotides, more preferably at least about 50 nucleotides, at least about 60 nucleotides, at least about 70 nucleotides, at least about 80 nucleotides, at least about 90 nucleotides, at least about 100 nucleotides, at least about 110 nucleotides, at least about 120 nucleotides, and most preferably at least about 130 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polynucleotides possess biological activities that are the same or similar to those of the inventive polypeptides or polynucleotides. The term "variant" with reference to polynucleotides and polypeptides encompasses all forms of polynucleotides and polypeptides as defined herein. Thus, "vesiculin variant(s)" include, for example, vesiculins having amino acid deletions or substitutions, including conservative amino acid substitutions, wherein one or more biological activities are retained, in whole or in part.

Variant polynucleotide sequences preferably exhibit at least about 50%, more preferably at least about 70%, more preferably at least about 80%, more preferably at least about 90%, more preferably at least about 95%, more preferably at least about 98%, and most preferably at least about 99% identity to a specified polynucleotide. Identity is found over a comparison window of at least about 20 nucleotide positions, preferably at least about 50 nucleotide positions, more preferably at least about 100 nucleotide positions or more of the entire length of a polynucleotide of the invention.

An exemplary family of programs useful for identifying variants in sequence databases is the BLAST suite of programs (version 2.2.5 [Nov. 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen. The use of the BLAST family of algorithms, including BLASTN, BLASTP, and BLASTX, is described in the publication of Altschul et al., *Nucleic Acids Res.* 25:3389-3402, (1997).

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

Polynucleotide sequence identity can be determined in the following manner. The subject polynucleotide sequence is compared to a candidate polynucleotide sequence using BLASTN (from the BLAST suite of programs, version 2.2.5 [Nov. 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences may be examined using the following UNIX command line parameters:

bl2seq -i nucleotideseq1 -x nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (for example Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Use of BLASTN as described above is preferred for use in the determination of sequence identity for polynucleotide variants according to the present invention.

Polynucleotide variants also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [Nov. 2002]) from NCBI (ftp://ftp.ncbi.nih.gov/blast/).

The similarity of polynucleotide sequences may be examined using the following UNIX command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. The BLASTN, BLASTP, BLASTX, tBLASTN and tBLASTX algorithms also produce "Expect" values for alignments. These programs find regions of similarity between the sequences and for each such region reports an Expect value (E value) which is the expected number of times one could expect to see such a match by chance in a database of a fixed reference size containing random sequences. The E value is used as a significance threshold for determining whether the hit to a database indicates true similarity. The size of this database is set by default in the bl2seq program. For small E values, much less than one, the E value is approximately the probability of such a random match. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Variant polynucleotide sequences preferably exhibit an E value of less than about $1\times10^{-5}$, more preferably less than about $1\times10^{-6}$, more preferably less than about $1\times10^{-9}$, more preferably less than about $1\times10^{-12}$, more preferably less than about $1\times10^{-15}$, more preferably less than about $1\times10^{-18}$ and most preferably less than about $1\times10^{-21}$ when compared with any one of the specifically identified sequences.

Alternatively, variant polynucleotides hybridize to the specified polynucleotide sequence, or a complement thereof under stringent conditions. The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C−log(Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as pre-washing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science 254(5037):1497-500 (1991)) Tm values are higher than those for DNA-DNA or DNA-RNA hybrids, and can be calculated using the formula described in Giesen et al., Nucleic Acids Res. 26(21):5004-6 (1998). Exemplary stringent hybridization conditions for a DNA-PNA hybrid having a length less than 100 bases are 5 to 10° C. below the Tm.

Variant polynucleotides also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation." Except for ATG (methionine) and TGG (tryptophan), other codons for the same amino acid may be changed by art recognized techniques, for example, to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, for example, Bowie et al., Science 247:1306 (1990)).

Variant polynucleotides due to silent variations and conservative substitutions in the encoded polypeptide sequence may be determined using the publicly available bl2seq program from the BLAST suite of programs (version 2.2.5 [Nov. 2002]) from NCBI (ftp://ftp.ncbi.nih.gov/blast/) via the tblastx algorithm as previously described.

Polypeptide sequence identity can also be determined in the following manner. The subject polypeptide sequence is compared to a candidate polypeptide sequence using BLASTP (from the BLAST suite of programs, version 2.2.5 [Nov. 2002]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X., "On Global Sequence Alignment," Computer Applications in the Biosciences 10:227-235 (1994)) as discussed above are also suitable global sequence alignment programs for calculating polypeptide sequence identity.

Use of BLASTP as described above is preferred for use in the determination of polypeptide variants according to the present invention.

Polypeptide variants also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [Nov. 2002]) from NCBI (ftp://ftp.ncbi.nih.gov/blast/). The similarity of polypeptide sequences may be examined using the following UNIX command line parameters:

bl2seq -i peptideseq1 -j peptideseq2 -F F -p blastp.

Variant polypeptide sequences preferably exhibit an E value of less than $1\times10^{-5}$, more preferably less than $1\times10^{-6}$, more preferably less than $1\times10^{-9}$, more preferably less than $1\times10^{-12}$, more preferably less than $1\times10^{-15}$, more preferably less than $1\times10^{-18}$ and most preferably less than $1\times10^{-21}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, for example, Bowie et al., 1990, Science 247, 1306).

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of DNA or RNA. Also included are vectors that provide more than one of the above functions. The vector may be capable of replication in at least one additional host system, such as E. coli.

The term "expression construct" refers to a genetic construct that includes the necessary elements that permit transcription of a polynucleotide molecule in a host, and, optionally, translating the transcript into a polypeptide. An "expression vector" is an example of an expression construct. An expression construct typically comprises in a 5' to 3' direction:
 a) a promoter functional in the host cell into which the construct will be transformed,
 b) the polynucleotide to be expressed, and
 c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequence to be expressed is placed under the control of regulatory elements that include promoters, tissue-specific regulatory elements, temporal regulatory elements, enhancers, repressors and/or terminators.

The term "noncoding region" refers to untranslated sequences that are upstream of the translational start site and downstream of the translational stop site. These sequences are also referred to respectively as the 5' UTR and the 3' UTR. These regions include elements useful for transcription initiation and termination and for regulation of translation efficiency.

Terminators are sequences that terminate transcription, and are typically found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "subject" refers to a vertebrate that is a mammal, for example, a human. Mammals include, but are not limited to, humans, farm animals, sport animals, pets, primates, mice and rats.

Peptides of the invention, including, for example, vesiculins and variants thereof may be generated by synthetic or recombinant means (i.e., single or fusion polypeptides). Polypeptides, especially shorter polypeptides up to about 50 amino acids, are conveniently made by chemical synthesis. See, for example, Atherton and Sheppard, "Solid Phase Peptide Synthesis: A Practical Approach," New York: IRL Press, 1989; Stewart and Young: "Solid-Phase Peptide Synthesis 2nd Ed.," Rockford, Ill.: Pierce Chemical Co., 1984; and Jones, "The Chemical Synthesis of Peptides," Oxford: Clarendon Press, 1994. For example, to be prepared synthetically, a vesiculin may be synthesized using peptide synthesis methods well known in the art such as direct peptide synthesis using solid phase techniques (for example Stewart et al., 1969, in Solid-Phase Peptide Synthesis, WH Freeman Co, San Francisco Calif.) or any of the commercially available solid phase techniques such as the Merrifield solid phase synthesis method, where amino acids are sequentially added to a growing amino acid chain (see, for example, Merrifield, *J. Am. Soc.* 85:2146-2149 (1963); Marglin, A. and Merrifield, R. B. *Annu. Rev. Biochem.* 39:841-66 (1970); and Merrifield R. B. JAMA. 210(7):1247-54 (1969)). Variations of the Merrifield solid phase synthesis, for example Fmoc, may also be used to chemically synthesize vesiculins, vesiculin chains, and vesiculin and vesiculin chain variants, derivatives and active fragments. Equipment for automated synthesis of peptides or polypeptides is also commercially available from suppliers such as Perkin Elmer/Applied Biosystems (Foster City, Calif.) and may be operated according to the manufacturers instructions. Mutated or variant forms of the polypeptides may also be produced during such syntheses. Confirmation of the identity of the newly synthesized vesiculin peptides and vesiculin variants may be achieved by amino acid analysis, mass spectroscopy, Edman degradation, or by assessing biological function (i.e., stimulating glucose incorporation into glycogen, or β-cell mitogenesis).

Variants of vesiculin may also be made by substituting amino acids which do not substantially alter the bioactivity of the vesiculin variant (e.g., conservative substitutions). Selection of amino acids for substitution can depend on the size, structure, charge, and can be either an amino acid found in nature or synthetic amino acid. Generally, amino acids which have a similar charge (e.g., hydrophobic for hydrophobic) or similar size (e.g., isoleucine for leucine) can be selected for substitution. One or more substitutions can be made in a stepwise fashion or concurrently. Variations in the residues included in the peptide are also both possible and contemplated. For example, it is possible to substitute amino acids in a sequence with equivalent amino acids using conventional techniques. Groups of amino acids known normally to be equivalent are:
 (a) Ala, Ser, Thr, Pro, and Gly;
 (b) Asn, Asp, Glu, and Gln;
 (c) His, Arg, and Lys;
 (d) Met, Glu, Ile, and Val; and
 (e) Phe, Tyr, and Trp.

The substitution of one amino acid for another in the same group as shown above is an example of a conservative amino acid substitution as used herein. Vesiculin variants produced by one or more conservative amino acid substitutions are herein termed "conservative variants."

It is understood that many vesiculin variants can be achieved by substituting one or more amino acids. The vesiculin variants can be tested for biological function, such as for example, to stimulate glucose incorporation into glycogen, whether in vivo or in vitro. The biological activity of a vesiculin variant is generally at least about 25% of a vesiculin, preferably at least about 35%, preferably at least about 50%, preferably at least about 60%, preferably at least about 75%, preferably at least about 85%, and more preferably at least about 95%.

The invention also encompasses active fragments with vesiculin bioactive functionality. Such active fragments may be obtained by deletion of one or more amino acid residues of full-length vesiculin. Active fragments or portions of vesiculin may be ascertained by stepwise deletions of amino acid residues, from the N-terminal end or the C-terminal end or from within the vesiculin peptide. If an amino acid is deleted and the bioactivity of vesiculin is not substantially reduced, then the amino acid may not comprise a portion of the active fragment. Further, polypeptides comprising an active fragment of vesiculin or vesiculin variant(s) are also encompassed in the invention. For example, active fragments of vesiculin may comprise about 10 contiguous amino acids of the amino acids of the amino acid sequence of either or both the A-chain and/or B-chain of vesiculin, more preferably about 15 contiguous amino acids, more preferably about 20 contiguous amino acids, more preferably about 25 contiguous amino acids, more preferably about 30 contiguous amino acids, about 40 contiguous amino acids, about 50 contiguous amino acids, about 60 contiguous amino acids, or more preferably 61 contiguous amino acids.

Additions and/or deletions of amino acids may also be made as long as the resulting peptide is immunologically cross-reactive with and/or has substantially the same function or functions as a vesiculin. The invention also encompasses polynucleotides which code for a vesiculin or an active fragment of a vesiculin. Polynucleotides which code for vesiculin variants or active fragments of vesiculin variants are also encompassed within the invention.

The polypeptides and variant polypeptides may also be isolated or purified from natural sources using a variety of techniques that are well known in the art (for example Deutscher, 1990, Ed, Methods in Enzymology, Vol. 182, Guide to Protein Purification).

Vesiculins, chains, fragments, and variants thereof may also be produced recombinantly by inserting a polynucleotide (usually DNA) sequence that encodes the protein into an expression vector and expressing the peptide in an appropriate host. A polynucleotide encoding the desired polypeptide, whether in fused or mature form, and whether or not containing a signal sequence to permit secretion, may be ligated into expression vectors suitable for any convenient host. Any of a variety of expression vectors (either eukaryotic or prokaryotic) known to those of ordinary skill in the art may be employed. Expression may be achieved in any appropriate host cell that has been transformed or transfected with an expression vector containing a DNA molecule which encodes the recombinant peptides. Suitable host cells include prokaryotes, yeasts and eukaryotic cells. Examples of prokaryotic host cells are known in the art and include, for example, *E. coli* and *B. subtilis*. Examples of eukaryotic host cells are known in the art and include yeast, avian, insect, plant, and animal cells such as COS 7, HeLa, CHO and other mammalian cells. Standard techniques for recombinant production are described for example, in Maniatis et al. Molecular Cloning—A Laboratory Manual, Cold Spring Harbour Laboratories, Cold Spring Harbour, New York (1989).

The polypeptide is then isolated from lysed cells or from the culture medium and purified to the extent needed for its intended use. Purification or isolation of the polypeptides expressed in host systems can be accomplished by any method known in the art. For example, cDNA encoding a polypeptide intact or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (e.g., for secretion), can also be used.

A fusion protein may also be constructed that facilitates purification. Examples of components for these fusion proteins include, but are not limited to myc, HA, FLAG, His-6, glutathione S-transferase, maltose binding protein or the Fc portion of immunoglobulin. These methods are known in the art. See, for example, Redd et al., *J. Biol. Chem.* 272:11193-11197 (1997).

If used for diagnostic purposes, the polypeptides are at least substantially purified or isolated from other cellular constituents. The polypeptides are preferably at least about 80% pure, and free of pyrogens and other contaminants. Methods of protein purification are known in the art and are not described in detail herein.

Host Cells Comprising Vesiculin Polynucleotides

Another embodiment of this invention are host cells transformed or transfected with (i.e., comprising) polynucleotides coding for a vesiculin, a vesiculin A chain, a vesiculin B chain, a vesiculin variant, a vesiculin derivative, and/or a vesiculin active fragment, vectors comprising such polynucleotides, or other vectors as described above. Both prokaryotic and eukaryotic host cells may be used. Prokaryotic hosts include bacterial cells, for example *E. coli* and *B. subtilis*. Among eukaryotic hosts are yeast, insect, avian, plant and mammalian cells. One example of a mammalian host cell is NS0, obtainable from the European Collection of Cell Cultures (England). Transfection of NS0 cells with a plasmid, for example, which is driven by a cytomegalovirus (CMV) promoter, followed by amplification of this plasmid provides a useful system for protein production. Cockett et al., *Bio/Technology* 8:662-667 (1990).

The host cells of this invention can be used, inter alia, as repositories of vesiculin polynucleotides and/or vehicles for production of vesiculin polynucleotides and polypeptides as described above. They may also be used as vehicles for in vivo delivery of vesiculin polypeptides.

Isolation of Vesiculin Polynucleotides

Vesiculin polynucleotides can be isolated from various sources including but not limited to host cells transformed (or transfected) with expression vector expressing vesiculin, biological samples or fluids, tissue samples (e.g., pancreas), or from a cloning vector. Isolation of nucleotides from cells is routine to a skilled artisan and may be achieved using any number of commercially available nucleotide isolation kits, for example from Qiagen (Valencia, Calif.) or Promega (Madison, Wis.), or using PCR-based methods (Mullis et al., Eds. 1994 The Polymerase Chain Reaction, Birkhauser). Typically, the polynucleotide sequence of a primer, useful to amplify variants of polynucleotide molecules by PCR, may be based on a sequence encoding a conserved region of the corresponding amino acid sequence. Polynucleotides encoding vesiculin and vesiculin related polypeptides may be in the form of DNA, RNA, DNA analogs, RNA analogs, or a hybrid of DNA-RNA. Polynucleotides can be single stranded or double stranded.

Equivalent polynucleotides include nucleic acid sequences that encode proteins equivalent to a vesiculin, etc., as defined above. Equivalent polynucleotides also include nucleic acid sequences that, due to the degeneracy of the nucleic acid code, differ from native polynucleotides in ways that do not affect the corresponding amino acid sequences.

A prediction of whether a particular polynucleotide or polypeptide is equivalent to or a variant of those given above can be based upon homology. Polynucleotide or polypeptide sequences may be aligned, and percentage of identical nucleotides in a specified region may be determined against another sequence, using computer algorithms that are publicly available, as described above, or by computer-based methods well-known to those skilled in the art, using public domain sequence alignment algorithms and sequence similarity search tools to search sequence databases (public domain databases include Genbank, EMBL, Swiss-Prot, PIR and others). See, for example, *Nucleic Acids Res.* 29:1-10; 11-16 (2001) for examples of online resources. Similarity searches retrieve and align target sequences for comparison with a sequence to be analyzed (i.e., a query sequence). Sequence comparison algorithms use scoring matrices to assign an overall score to each of the alignments.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, (http://www-igbmc.u-strasbg.fr/BioInfo/ClustalW/Top.html) or T-COFFEE (Cedric Notredame, Desmond G. Higgins, Jaap Hering a, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Proteins can be classified according to their sequence relatedness to other proteins in the same genome (paralogues) or a different genome (orthologues). Orthologous genes are genes that evolved by speciation from a common ancestral gene and normally retain the same function as they evolve. Paralogous genes are genes that are duplicated within a genome and genes may acquire new specificities or modified functions which may be related to the original one. Phylogenetic analysis methods are reviewed in Tatusov, et al., 1997, Science 278, 631-637,).

In addition to the computer/database methods described above, polypeptide variants may be identified by physical methods, for example by screening expression libraries using antibodies raised against polypeptides of the invention (Sambrook, et al., Molecular Cloning: A Laboratory Manual, 2nd Ed. Cold Spring Harbor Press, 1987) or by identifying polypeptides from natural sources with the aid of such antibodies.

Polypeptides, including variant polypeptides, may be prepared using peptide synthesis methods well known in the art, as described above. The polypeptides and variant polypeptides may also be purified by any method known in the art, as described above. Alternatively the polypeptides and variant polypeptides may be expressed recombinantly in suitable host cells and separated from the cells as discussed above.

Variants according to the invention also include the homologues of vesiculin from species other than human, rat or mouse. Such homologues can be readily identified using, for example, nucleic acid probes based upon the conserved regions of the polynucleotides which encode human, rat and mouse vesiculin.

The polynucleotides of this invention have several uses. Vesiculin polynucleotides are useful, for example, in expression constructs and systems for the recombinant production of a vesiculin or vesiculin fragments. They are also useful as hybridization probes to assay for the presence of vesiculin polynucleotide (or related) sequences in a sample using methods well known to those in the art. Further, vesiculin polynucleotides are also useful as primers to effect amplification of desired polynucleotides. The polynucleotides of this invention may be also useful as vaccines and for gene therapy.

Vesiculin polynucleotides of this invention can be used as primers for amplification of polynucleotides encoding vesiculin or a fragment thereof, such as in a polymerase chain reaction (PCR). Further, the vesiculin polynucleotides can be also used as PCR primers to screen for or to detect other genes associated with vesiculin or genes related to disease or disease states which are also associated with vesiculin. The conditions for carrying out PCR reactions depend on the specificity desired, which in turn can be adjusted by the primer used and the reaction conditions. Such adjustments are known in the art and need not be discussed in detail herein.

Vesiculin polynucleotides can also be used as hybridization probes for detection of, for example, the presence of vesiculin polynucleotides in a cell. For instance, a vesiculin polynucleotide could be used as a probe to determine the presence of vesiculin polynucleotide sequences in cells used in gene therapy. For these methods, suitable cells from a biological sample or a sample derived from cells (either of which are suspected of containing vesiculin polynucleotide sequences) is obtained and tested for the presence of a vesiculin polynucleotide by contacting the polynucleotides from the sample with the vesiculin polynucleotide probe. The method is conducted to allow hybridization to occur between the vesiculin probe and vesiculin polynucleotide of interest, and the resultant (if any) hybridized complex is detected. Such methods entail procedures well known in the art, such as cell culture, polynucleotide preparation, hybridization, and detection of hybrid complexes formed, if any. For example, the technique of hybridizing labeled polynucleotide probes to polynucleotides immobilized on solid supports such as nitrocellulose filters or nylon membranes, can be used to screen, for example, genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C. Using similar methods, the probes can also be used to detect vectors which are in turn used to produce vesiculin polypeptides, intact vesiculin, or recombinant, variant forms of vesiculin.

The vesiculin polynucleotides of this invention can be used in expression constructs and systems to produce vesiculin polypeptides, intact vesiculin, or recombinant forms of vesiculin, including intact vesiculin, which have enhanced, equivalent, or different, desirable properties. These recombinant forms are made by using methods disclosed supra or other routine methods in the art. Examples of recombinant forms of vesiculin and vesiculin polypeptides include, but are not limited to, hybrids, chimeras, single chain variants, and fusion proteins containing other components such as cytokines.

Another use of vesiculin polynucleotides is in gene therapy. One general principle is to administer the polynucleotide so that it either promotes or attenuates the expression of the polypeptide encoded therein. Thus, the present invention includes methods of modulating blood glucose levels and methods of treatment comprising administration of an effective amount of a vesiculin polynucleotide(s) to an individual. In these methods, a vesiculin polynucleotide encoding a vesiculin polypeptide is administered to an individual, either directly or via cells transfected with the vesiculin polynucleotide(s). In one embodiment the vesiculin polynucleotide is replicated inside a cell. Thus, the vesiculin polynucleotide(s) is operatively linked to a suitable promoter, such as a heterologous promoter that is intrinsically active in cells of the target tissue type. Entry of the polynucleotide into the cell is accomplished by techniques known in the art, such as via a viral expression vector, such as a vaccinia or adenovirus vector, or association of the polynucleotide with a cationic liposome. The vesiculin polynucleotide(s) may be in the form of a circular plasmid or in a supercoiled configuration. Once in cell nuclei, plasmids persist as circular non-replicating episomal molecules. Attenuation or inhibition of the expression of the vesiculin polypeptide may be achieved by known art methods such as administration of a nucleic acid that inhibits or antagonises the expression of the vesiculin polypeptide. Antisense oligonucleotides, siRNA, or ribozymes which disrupt expression of the vesiculin polypeptide can all be used for inhibiting expression.

Antisense-oligonucleotides corresponding to any of the nucleotide sequence of vesiculin can be used to reduce the expression level of vesiculin. Specifically, anti sense-oligonucleotides of the present invention may act by binding to any of the polypeptides encoded by vesiculin or mRNAs corresponding thereto, thereby inhibiting the transcription or translation of the vesiculin polypeptide, promoting the degradation of the mRNAs, and/or inhibiting the expression of proteins encoded by the vesiculin nucleotides, and finally inhibiting the function of the proteins. The term "antisense-oligonucleotides" as used herein encompasses both nucleotides that are entirely complementary to the target sequence and those having a mismatch of one or more nucleotides, so long as the antisense-oligonucleotides can specifically hybridize to the target sequence. For example, the antisense-oligonucleotides of the present invention include polynucleotides that have an identity of at least about 70% or higher, preferably at about 80% or higher, more preferably about 90% or higher, even more preferably about 95% or higher over a span of at least about 15 continuous nucleotides to any of the nucleotide sequence of vesiculin. Algorithms known in the art as discussed above can be used to determine the identity. Furthermore, derivatives or modified products of the antisense-oligonucleotides can also be used as antisense-oligonucleotides in the present invention. Examples of such modified products include lower alkyl phosphonate modifications such as methyl-phosphonate-type or ethyl-phosphonate-type, phosphorothioate modifications and phosphoroamidate modifications.

The antisense-oligonucleotides and derivative, thereof act on cells producing the proteins encoded by vesiculin by binding to the DNAs or mRNAs encoding the proteins, inhibiting their transcription or translation, promoting the degradation of the mRNAs and inhibiting the expression of the proteins, thereby resulting in the inhibition of the protein function.

The nucleic acids that attenuate or inhibit gene expression also include small interfering RNAs (siRNA) comprising a combination of a sense strand nucleic acid and an antisense strand nucleic acid of the nucleotide sequence encoding a vesiculin polypeptide. The term "siRNA" refers to a double stranded RNA molecule which prevents translation of a target mRNA. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, for example, a hairpin.

The method is used to suppress gene expression of a cell with up-regulated expression of a vesiculin polypeptide. Binding of the siRNA to the vesiculin marker transcript in the target cell results in a reduction of vesiculin polypeptide production by the cell. The length of the oligonucleotide is at least about 10 nucleotides and may be as long as the naturally occurring transcript. Preferably, the oligonucleotide is about 19-25 nucleotides in length. Most preferably, the oligonucleotide is less than about 75, less than about 50 or less than about 25 nucleotides in length.

The nucleotide sequence of siRNAs may be designed using a siRNA design computer program available from the Ambion website (http:/lwww.ambion.com/techlib/misc/siRNA_finder.html). Nucleotide sequences for the \ siRNA are selected by the computer program based on the following protocol:

Selection of siRNA Target Sites:

1. Beginning with the AUG start codon of transcript, scan downstream for AA dinucleotide sequences. Record the occurrence of each AA and the 3' adjacent 19 nucleotides as potential siRNA target sites. Tusehi, et al. recommend not to design siRNA against the 5' and 3' untranslated regions (UTRs) and regions near the start codon (within 75 bases) as these may be richer in regulatory protein binding sites, and thus the complex of endonuclease and siRNAs that were designed against these regions may interfere with the binding of UTR-binding proteins and/or translation initiation complexes.

2. Compare the potential target sites to the human genome database and eliminate from consideration any target sequences with significant homology to other coding sequences. The homology search can be performed using BLAST, which can be found on the NCBI server at: www.ncbi.nlm.nih.govIBLAST/

3. Select qualifying target sequences for synthesis. On the website of Ambion, several preferable target sequences can be selected along the length of the gene for evaluation.

The siRNAs inhibit the expression of vesiculin polypeptide and is thereby useful for suppressing the biological activity of the protein. Therefore, a composition comprising the siRNA is useful in treating or preventing conditions in which the activity of vesiculin in implicated.

The nucleic acids that inhibit one or more gene products of overexpressed genes also include ribozymes against the overexpressed markers.

The ribozymes inhibit the expression of vesiculin polypeptide and is thereby useful for suppressing the biological activity of the protein. Therefore, a composition comprising the ribozyme is useful in treating or preventing conditions in which the activity of vesiculin in implicated.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi, et al., FEBS Lett. 228: 225 (1998)) and hairpin type ribozymes (Buzayan, Nature 323: 349 (1986); Kikuchi and Sasaki, Nucleic Acids Res. 19: 6751 (1992)) are included in the small ribozymes. Methods for designing and constructing ribozymes are known in the art (see Koizumi, et al., supra; Koizumi, et al., Nucleic Acids Res. 17: 7059 (1989); Kikuchi and Sasaki, supra) and ribozymes inhibiting the expression of vesiculin polypeptide can be constructed based on the sequence information of the nucleotide sequence encoding the vesiculin polypeptide according to conventional methods for producing ribozymes.

The ribozymes inhibit the expression of vesiculin polypeptide and is thereby useful for suppressing the biological activity of the protein. Therefore, a composition comprising the ribozyme is useful in treating or preventing conditions in which the activity of vesiculin in implicated.

Alternatively, the function of one or more gene products of the over-expressed genes is inhibited by administering a compound that binds to or otherwise inhibits the function of the gene products. For example, the compound is an antibody which binds to the over-expressed marker product or products.

Administration of Vesiculin

The invention includes methods for treating and/or preventing, in whole or in part, various diseases, disorders, and conditions, including for example, impaired glucose tolerance; impaired fasting glucose; prediabetes; diabetes and/or its complications, including type 1 and type 2 diabetes and their complications; insulin resistance; Syndrome X; obesity and other weight related disorders; fatty liver disease, including nonalcoholic alcoholic fatty liver disease; glucose metabolism diseases and disorders; diseases, disorders or conditions that are treated or treatable with insulin; diseases, disorders or conditions that are treated or treatable with a hypoglycemic agent; diseases, disorders, and conditions characterized at least in part by hyperglycemia; diseases, disorders, and conditions characterized at least in part by hypoinsulinemia and/or diseases, disorders, and conditions characterized at least in part by hyperinsulinemia.

The invention includes methods for treating a subject having or suspected of having or predisposed to, or at risk for, for example, any diseases, disorders and/or conditions characterized in whole or in part by hyperglycemia, insulin resistance, impaired glucose tolerance, and/or impaired fasting glucose, comprising administering a composition comprising a vesiculin, a vesiculin A chain, a vesiculin B chain, a vesiculin variant, a vesiculin derivative and/or a vesiculin fragment or a salt thereof. Such diseases, disorders and/or conditions include but are not limited to those described or referenced herein. Such compounds may be administered in amounts, for example, that are effective to (1) lower serum glucose, (2) lower blood glucose, (3) lower urine glucose, (4) lower fructosamine, (5) lower glycosylated hemoglobin (HbA$_{1c}$) levels, (6) lower postprandial glycemia, (7) ameliorate impaired glucose tolerance, (8) ameliorate impaired fasting glucose, (9) lower the rate and/or severity of hypoglycemic events, including severe hypoglycemic events, and/or (10) and/or stimulate glucose disposal. Such compositions include, for example, formulations for delivery by injection, transdermal patch, inhalation, and other non-oral delivery methods.

The invention includes methods for regulating glycemia in a subject having or suspected of having or predisposed to diseases, disorders and/or conditions characterized in whole or in part, for example, by hyperglycemia, insulin resistance, impaired glucose tolerance, and/or impaired fasting glucose, comprising administering a composition comprising a vesiculin, a vesiculin A chain, a vesiculin B chain, a vesiculin variant, a vesiculin derivative and/or a vesiculin fragment or a salt thereof. Such diseases, disorders and/or conditions include but are not limited to those described or referenced herein. Such compounds may be administered in amounts, for example, that are effective to (1) lower serum glucose, (2) lower blood glucose, (3) lower urine glucose, (4) lower fructosamine, (5) lower glycosylated hemoglobin (HbA$_{1c}$) levels, (6) lower postprandial glycemia, (7) ameliorate impaired glucose tolerance, (8) ameliorate impaired fasting glucose, (9) lower the rate and/or severity of hypoglycemic events, including severe hypoglycemic events. Such compositions include, for example, formulations for delivery by injection, transdermal patch, inhalation, and other non-oral delivery methods, and/or (10) stimulate glucose disposal.

For administration to a patient, a vesiculin, a vesiculin A chain, a vesiculin B chain, a vesiculin variant, a vesiculin derivative, and/or a vesiculin active fragment, or salts thereof may be used in pure or substantially pure form. Vesiculins, vesiculin A chains, vesiculin B chains, vesiculin variants, vesiculin derivatives, and/or vesiculin active fragments, or salts thereof, may be presented as a pharmaceutical composition. Such compositions may comprise one or more of a vesiculin, a vesiculin A chain, a vesiculin B chain, a vesiculin variant, a vesiculin derivative, and/or a vesiculin active fragment, or salts thereof, for example, together with one or more pharmaceutically acceptable carriers and optionally other ingredients where desirable. Formulations for parenteral and non parenteral drug delivery are known in the art and are set forth, for example, in Remington's Pharmaceutical Sciences, 18th Edition, Mack Publishing (1990).

The carrier is acceptable in the sense of being compatible with the peptide being administered and not overtly harmful to the subject to be treated. Desirably, the composition should not include substances with which peptides are known to be incompatible. For solid compositions, conventional nontoxic carriers include, for example mannitol, lactose, starch, magnesium stearate, magnesium carbonate, sodium saccharin, talcum, cellulose, glucose, sucrose, pectin, dextrin, tragacanth, methyl cellulose, sodium carboxymethyl cellulose, a low-melting wax, cocoa butter, and the like may be used. The active compound as defined above may be formulated as suppositories using, for example, polyalkylene glycols, for example, propylene glycol as a carrier.

A solid carrier can be one or more substances which may also act as diluents, flavoring agents, solubilizers, lubricants, suspending agents, binders, or tablet disintegrating agents; it can also be an encapsulating material. In a similar manner, cachets or transdermal systems are included. In powders, the carrier is a finely divided solid which is in a mixture with the finely divided active component. In tablets, the active component is mixed with the carrier having the necessary binding properties in suitable proportions and compacted in the shape and size desired.

Liquid form preparations include solutions, suspensions, or emulsions suitable, for example, for parenteral administration. Aqueous solutions for parenteral administration can be prepared by dissolving the subject peptide in water and adding other suitable agents, stabilizers, buffers, etc., as desired. Actual methods of preparing such dosage forms are known, or will be apparent to those skilled in this art; for example, see Remington's Pharmaceutical Sciences.

The composition or formulation to be administered will preferably contain a quantity of the active compound in an amount effective to (1) lower serum glucose, (2) lower blood glucose, (3) lower urine glucose, (4) lower fructosamine, (5) lower glycosylated hemoglobin ($HbA_{1c}$) levels, (6) lower postprandial glycemia, (7) ameliorate impaired glucose tolerance, (8) ameliorate impaired fasting glucose, (9) lower the rate and/or severity of hypoglycemic events, including severe hypoglycemic events, and/or (10) stimulate glucose disposal. An effective amount of a vesiculin, a vesiculin A chain, a vesiculin B chain, a vesiculin variant, a vesiculin derivative, and/or a vesiculin active fragment, or a salt thereof may include, for example, from about 0.01 nmol/kg/day to about 100 nmol/kg/day, from about 0.02 nmol/kg/day to about 75 nmol/kg/day, from about 0.025 nmol/kg/day to about 50 nmol/kg/day, from about 0.03 nmol/kg/day to about 40 nmol/kg/day, from about 0.04 nmol/kg/day to about 30 nmol/kg/day, from about 0.05 nmol/kg/day to about 25 nmol/kg/day, from about 0.07 nmol/kg/day to about 20 nmol/kg/day, from about 0.08 nmol/kg/day to about 15 nmol/kg/day, from about 0.1 nmol/kg/day to about 10 nmol/kg/day, from about 0.2 nmol/kg/day to about 5 nmol/kg/day.

An effective amount of a vesiculin, a vesiculin A chain, a vesiculin B chain, a vesiculin variant, a vesiculin derivative, and/or a vesiculin active fragment, or a salt thereof may also include, for example, from about 120 ng/kg/day to about 1.2 mg/kg/day, from about 240 ng/kg/day to about 900 µg/kg/day, from about 300 ng/kg/day to about 600 µg/kg/day, from about 360 ng/kg/day to about 480 µg/kg/day, from about 480 ng/kg/day to about 400 µg/kg/day, from about 600 ng/kg/day to about 300 µg/kg/day, from about 840 µg/kg/day to about 240 µg/kg/day, from about 960 ng/kg/day to about 180 µg/kg/day, from about 1.2 µg/kg/day to about 120 µg/kg/day, and from about 2.4 µg/kg/day to about 60 µg/kg/day.

It is understood that the dosage administered may vary from individual to individual. It is also understood that the dosage may be administered in a single dose or optionally multiple doses (e.g., two, three, or four doses per day). A clinician or physician will determine the dosage needed for individuals. A clinician or physician may monitor factors including but not limited to glucose level, vesiculin level (either circulating or resident in tissues), insulin levels (either circulating or resident in tissues), level of depletion of pancreatic β-cells, presence or absence of polydipsia, presence or absence of polyphagia, presence or absence of polyuria, levels of glycated hemoglobin, levels of glycated albumin, and levels of fructosamine.

The compositions may conveniently be presented in unit dosage form and may be prepared by any of the methods well known in the art of pharmacy. All methods include the step of bringing the active ingredients into association with a carrier which constitutes one or more accessory ingredients.

The precise form the composition will take will largely be dependent upon the administration route chosen. For example, a vesiculin, a vesiculin A chain, a vesiculin B chain, a vesiculin variant, a vesiculin derivative, and/or a vesiculin active fragment, may be injected parenterally, for example, intravenously into the blood stream of the patient being treated. However, it will be readily appreciated by those skilled in the art that the route can vary, and can be intravenous, subcutaneous, transcutaneous, intramuscular, intradermal, intraarticular, intrathecal, intraperitoneal, enterally, transdermally, transmucously, sustained release polymer compositions (for example a lactide polymer or co-polymer microparticle or implant), perfusion, pulmonary (for example, inhalation), nasal, oral, etc. Injectables can be prepared in conventional forms, either as liquid solutions or suspension, solid forms suitable for solution or suspension in liquid prior to injection, or as emulsions. Suitable excipients include, for example, water, saline, aqueous dextrose, glycerol, ethanol or the like. In addition, if desired, the pharmaceutical compositions may also contain minor amounts of non-toxic substances such as wetting or emulsifying agents, auxiliary pH buffering agents and the like, for example, sodium acetate, sorbitan monolaurate, triethanolamine oleate, etc. Compositions suitable for parenteral and in particular subcutaneous administration are preferred. Other suitable administration routes are intravenous administration and intramuscular administration. Such compositions conveniently comprise sterile aqueous solutions of a vesiculin, a vesiculin A chain, a vesiculin B chain, a vesiculin variant, a vesiculin derivative, and/or a vesiculin active fragment, or a salt thereof. The solutions can be isotonic with the blood of the patient to be treated. Such compositions may be conveniently prepared by dissolving a vesiculin, a vesiculin A chain, a vesiculin B chain, a vesiculin variant, a vesiculin derivative, and/or a vesiculin active fragment, or a salt thereof in water to produce an aqueous solution and rendering this solution sterile. The composition may then be presented in unit or multi-dose containers, for example sealed ampoules or vials. One particularly preferred composition is a vesiculin, for example, a human vesiculin, in a physiological buffered solution suitable for injection.

Compositions suitable for sustained release parenteral administrations (e.g. biodegradable polymer formulations) are also well known in the art. See, for example, U.S. Pat. Nos. 3,773,919 and 4,767,628 and PCT Publication No. WO 94/15587.

It is envisaged oral delivery forms are equally acceptable, one example of oral delivery forms of tablet, capsule, lozenge, or the like form, or any liquid form such as syrups, aqueous solutions, emulsion and the like, capable of protecting the therapeutic protein from degradation prior to eliciting an effect, e.g., in the alimentary canal if an oral dosage form. Examples of dosage forms for transdermal delivery include transdermal patches, transdermal bandages, and the like.

Included within the topical dosage forms are any lotion, stick, spray, ointment, paste, cream, gel, etc., whether applied directly to the skin or via an intermediary such as a pad, patch or the like.

Examples of dosage forms for suppository delivery include any solid or other dosage form to be inserted into a bodily orifice (particularly those inserted rectally, vaginally and urethrally).

Examples of dosage units for transmucosal delivery include depositories, solutions for enemas, pessaries, tampons, creams, gels, pastes, foams, nebulised solutions, powders and similar formulations containing in addition to the active ingredients such carriers as are known in the art to be appropriate.

Examples of dosage units for depot administration include pellets or small cylinders of active agent or solid forms wherein the active agent is entrapped in a matrix of biodegradable polymers, microemulsions, liposomes or is microencapsulated.

Examples of implantable infusion devices include any solid form in which the active agent is encapsulated within or dispersed throughout a biodegradable polymer or synthetic, polymer such as silicone, silicone rubber, silastic or similar polymer. Alternatively dosage forms for infusion devices may employ liposome delivery systems.

Examples of dosage units for delivery via bolus include single or multiple administrations by intravenous injection, subcutaneous, subdermal, and intramuscular administration or oral administration.

Examples of dosage units for inhalation or insufflation include compositions comprising solutions and/or suspensions in pharmaceutically acceptable, aqueous, or organic solvents, or mixtures thereof and/or powders.

It is also convenient for vesiculin to be converted to be in the form of a salt. Such a salt will generally be physiologically acceptable, and can be formed using any method well known in the art. Pharmaceutically acceptable salts include those derived from pharmaceutically acceptable non-toxic inorganic and organic acids and bases. Examples of suitable acid salts include acetate, adipate, alginate, aspartate, benzoate, benzenesulfonate, benzoic, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, gluconic, glutamic, hemisulfate, heptanoate, hexanoate, hydrochloride, hydrobromide, hydroiodide, 2-hydroxyethanesulfonate, isethionic, lactate, maleate, malonate, malic, mandelic, methanesulfonate, mucic, 2-naphthalenesulfonate, nicotinate, nitrate, palmoate, pantothenic, pectinate, persulfate, 3-phenylpropionate, phosphate, picrate, pivalate, propionate, salicylate, succinate, sulfate, tartrate, thiocyanate, tosylate, undecanoate and the like. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Hydrochloride and acetate salts are preferred.

Vesiculin salts formed by combination of vesiculin with anions of organic acids are particularly preferred. Such salts include, but are not limited to, malate, acetate, propionate, butyrate, oxaloacetate, citrate, isocitrate, α-ketoglutarate, succinate, fumarate and trifluoroacetate salts. The salts thus formed can also be formulated into pharmaceutical compositions for therapeutic administration where desired.

Methods for Using Vesiculin Polynucleotides

As described above, the present invention provides a vesiculin and vesiculin A and B chains (including but not limited to their human, rat and mouse forms), a vesiculin variant, or a vesiculin derivative, or active fragment thereof. Vesiculins are shown herein to play a role, for example, in the stimulation of glucose incorporation into glycogen.

The invention therefore also provides methods by which glucose incorporation into glycogen can be modulated. Such modulation will usually involve administration of a vesiculin or vesiculin-related polypeptide as described herein.

A vesiculin agonist is a compound which can, for example, promote or potentiate the effect of vesiculin on glucose incorporation into glycogen. In contrast, a vesiculin antagonist is a compound which competes with vesiculin or otherwise interacts with vesiculin to block or reduce the effect of vesiculin, for example, on glucose incorporation into glycogen. Vesiculin agonists and antagonists can be identified by assay systems, including the soleus muscle assay, which measure the effect vesiculin has on glucose incorporation into glycogen in the presence and absence of a test compound.

Where it is desired that a vesiculin agonist or vesiculin antagonist be employed in modulating, for example but not limited to, glucose incorporation into glycogen, the agonist/antagonist can be administered as a substantially pure compound or formulated as a pharmaceutical composition as described above for vesiculin.

Other uses for vesiculin polypeptides include use in vaccines and for generation of antibodies, including monoclonal antibodies. Vesiculin polypeptides are used as immunogens to immunize mice. Splenocytes (including lymphocytes) are obtained from the immunized mice. Hybridomas are prepared from the lymphocytes and immortalized myeloma cells using the general somatic cell hybridization technique of Kohler, B. and Milstein, C., *Nature* 256:495-497 (1975). Other modified methods, for example by Buck, D. W., et al., *In Vitro* 18:377-381 (1982) may also be used. Available myeloma lines, include but are not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein, supplemented with or without serum, can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbants made of the immunogen attached to a solid phase and eluting or releasing the desired antibodies off the immunogen.

Vesiculin and vesiculin-related polypeptides, including vesiculin fragments, may also be used as immunogens to immunize other animals (e.g., rats and rabbits) to generate polyclonal antibodies. Methods of producing polyclonal antibodies and the subsequent isolation and purification thereof are well known in the art. See, for example, Harlow et al., supra. Other suitable techniques for preparing antibodies involve in vitro exposure of lymphocytes to the antigen or alternatively to selection of libraries of antibodies in phage or similar vectors. Also, recombinant antibodies may be produced using procedures known in the art. See, for example, U.S. Pat. No. 4,816,567.

The antibodies may be used with or without modification. Frequently, antibodies will be labeled by joining, either covalently or non-covalently a substance which provides a detectable signal. A wide variety of labels and conjugation techniques are known and are reported extensively in the literature.

Antibodies can be used to monitor the presence of vesiculin in a patient or in vesiculin quantification assays. Further, anti-vesiculin antibodies, for example, can be used to measure levels of vesiculin in an individual, either at one fixed time point or over a period of time to monitor fluctuations in circulating vesiculin levels. Anti-vesiculin antibodies can also be used to measure levels of vesiculin in an individual to whom drugs have been administered. In such assays, any convenient immunological format can be employed. Such formats include immunohistochemical assays, RIA, IRMA and ELISA assays.

The assays can be conducted in relation to any biological fluid which does, or should, contain vesiculin. Such fluids include blood, serum, plasma, urine and cerebrospinal fluid.

Antibodies, monoclonal or polyclonal, against vesiculin may be used for diagnosis or for therapeutic purposes. Antibodies may be used by themselves or attached to a solid substrate, such as a column or a plate. Antibodies which are attached to a solid substrate may be used for assays, for example ELISA, or as a standard in other assays. Antibodies against vesiculin are also useful for vesiculin isolation, vesiculin purification, and vesiculin quantitation.

The antibodies can also be included in assay kits. Such kits can contain, in addition, a number of optional but conventional components, the selection of which will be routine to the art skilled worker. Such additional components will however generally include a vesiculin reference standard, which may be vesiculin itself or a variant (such as a fragment).

It will also be appreciated that antibodies such as described above can be used as vesiculin antagonists by binding to vesiculin and partly or completely interfering with vesiculin activity.

As indicated above, the findings herein regarding vesiculin also have diagnostic implications. For example, individuals whose vesiculin production is less than is required in order to elicit, for example, glucose incorporation into glycogen, or who produce vesiculin in a less active or inactive (mutant) form will require therapeutic intervention. Diagnostic or prognostic methods are therefore within the scope of the invention.

In one embodiment, a diagnostic or prognostic method will involve detection of mutations in the gene coding for vesiculin and/or the vesiculin secretory mechanism. Detection can occur using any one of a number of art standard techniques including Single Stranded Confirmation Analysis (Orita et al. (1989)) or the Amplification Refractory Mutation System (ARMS) as disclosed in European Patent Application Publication No. 0 332 435.

If a mutation is detected, corrective approaches become possible. These include but are not limited to replacement therapy and gene therapy.

Compositions useful in the invention are prepared by mixing the ingredients following generally accepted procedures. For example, the selected components may be mixed in a blender or other standard device to produce a concentrated mixture which may then be adjusted to the final concentration and viscosity by the addition of water or thickening agent and possibly a buffer to control pH or an additional solute to control tonicity. Other applications relating to the discovery of vesiculin will be apparent to those persons skilled in the art, who will appreciate that the above description is provided by way of example only and that the invention is not limited thereto.

A better understanding of the invention will be gained by reference to the following non-limiting experimental section which is illustrative and are not intended to limit the invention or the claims in any way.

EXAMPLE 1

In this example vesiculin was isolated using the following materials, including βTC6-F7 cells. Optiprep™ was obtained from Total Lab Systems, the New Zealand distributors for Axis-Shield products. Acetonitrile used was either HiperSolv grade from BDH or UltimAR grade from Mallinckrodt. Trifluoroacetic acid (Protein Sequencer Grade TFA) was obtained from Applied Biosystems. The 5 µm Jupiter C18 column, 250×2.0 mm was purchased from Phenomenex. Mass spectrometry standards consisted of insulin (RP-HPLC purified from Actrapid® Recombinant Human Insulin [Novo Nordisk Pharmaceuticals]), and synthetic somatostatin (H-2260) purchased from Bachem. The MS matrix used was α-cyano-4-hydroxycinnamic acid (α-CHC) and was obtained from Hewlett Packard. Guanadine HCl, iodoacetic acid, modified RPMI (R1383) and Dulbecco's modified Eagles medium (DMEM; D5523) was purchased from Sigma while fetal bovine serum was sourced from Invitrogen. Dithiothreitol was purchased from Boehringer and sequencing-grade endoproteinase Asp-N was from Roche (1 420 488). $^{14}$C-glucose was from American Radiolabelled Chemicals and scintillant used was Starscint from Packard. All other chemicals used were analytical grade.

The methods employed for isolating vesiculin included the following:

Isolation of β-cell Secretory Granules—Secretory granules were isolated from mouse βTC6-F7 cells by ultracentrifugation on an OptiPrep™ gradient supplemented with Complete® Protease inhibitor (Roche) as follows and stored at −80° C.

Vesiculin was identified using a single step gradient-density centrifugal method to purify secretory granules from βTC6-F7 cells (passages 55-60 cultured in nDMEM with 15% heat-inactivated horse-serum and 2.5% FBS). The cells were harvested by trypsinization (2.5-4.0-ml cells), washed and suspended in homogenisation medium (Hutton J., et al., Diabetalogia 2:365-373 (1982)) and homogenised on ice (24 strokes, ball bearing homogeniser (Martin T., Methods in Enzymology 68:225-233 (1989)) before centrifugation (400 g, 10-min, 4° C.). Supernatants were overlaid on pre-formed continuous gradients (13%-31% OptiPrep™ (Nycomed) v/v in homogenisation medium) and ultra centrifuged (SW40Ti; 160,000 g; 16-h; 4° C.). Gradient-tubes were top-fractionated (HakkeBuchler Auto Densi-Flow II) and fractions containing granules combined (buoyant density 1.10-1.11). Purity was confirmed by protein/enzyme-marker assays: aryl sulphatase (lysosomes) (Chang, et al., *Anal. Biochem.* 117:382-389 (1981)); citrate synthase (mitochondria) (Srere, *Methods in Enzymology* 13:3-5 (1969)); insulin (granules). Insulin was used to track purification of granule-cores, whereas amylin, which is present in the granule-matrix (Johnson, et al., *Am. J. Pathol.* 130:1-8 (1988)), was measured to verify granule integrity. Granule integrity was also confirmed using RIAs for insulin (granule-core) and amylin (granule-matrix). See FIG. 1A.

Purification of Granule Proteins After Isolation—β-cell granules were thawed and centrifuged at 16000 g for 3 minutes before supernatant was semi-purified by reversed phase HPLC (RP-HPLC). HPLC system consisted of 140B Solvent Delivery System, 785A Programmable Absorbance Detector and 112A set at 214 nm, Oven/Injector set at 37° C. (Applied Biosystems) with Jupiter C18 column. Peptides were eluted after a 15 minute isocratic period at 10% buffer B (buffer A: 0.08% TFA v/v in $H_2O$; buffer B: 80% acetonitrile with 20% A; 250 µl·$min^{-1}$). Elution conditions utilized a gradient from 10-60% buffer B over 25 minutes. Co-eluting peaks were speed-vac concentrated to remove acetonitile and then re-injected and resolved by further RP-HPLC separation on a very flat gradient (0.5% buffer B/minute).

EXAMPLE 2

This Example relates to the identification and characterization of a vesiculin.

Identification of Granule Proteins—Peptides eluted from RP-HPLC were subjected to N-terminal sequencing on an Applied Biosystems Procise™ 492 protein sequencer using chemicals supplied by the manufacturer (Applied Biosystems).

Figure 1B:
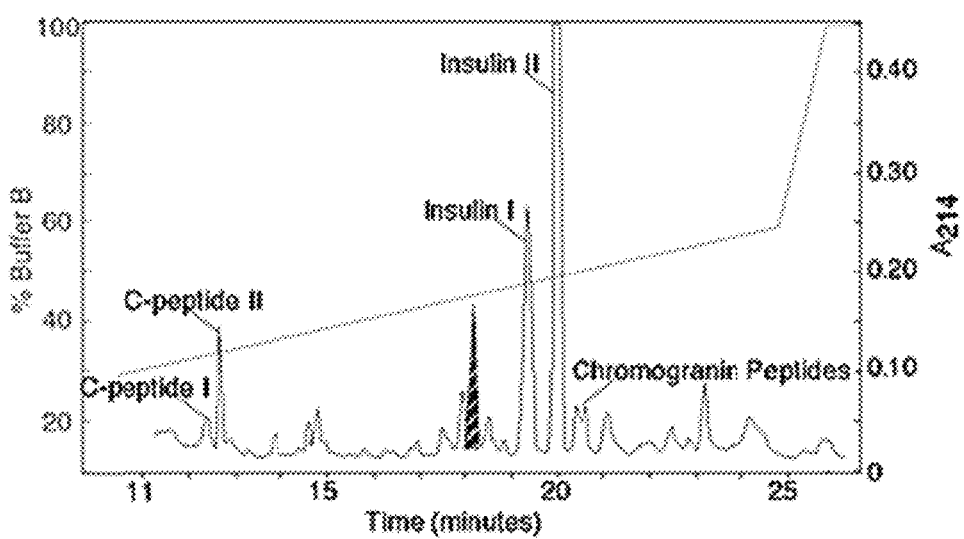

Molecular Weight Determination—Molecular weights of purified proteins were determined by MALDI-TOF mass spectrometry (Hewlett Packard G2025A). Samples and external standards (10 µM insulin and somatostatin) were mixed 1:1 with α-CHC (33 mM in 1:2 mixture of acetonitrile:1.33% TFA) and co-crystallised after vacuum drying (Hewlett Packard G2024A Sample prep accessory). Mass/charge ratios (m/z) of unknown proteins were generated by accumulating the data from 50 laser shots (Table 1). In this manner, the presence of C-peptide I and II fragments, amylin, ubiquitin, preptin, an IGF-II-like peptide, insulins I and II, neuropeptide Y, chromogranin A, and calreticulin (FIG. 1B and Table 1) was confirmed. Masses were obtained for all peptides except ubiquitin, neuropeptide Y, chromogranin A and calreticulin, possibly because these proteins were in lower abundance and of a higher molecular weight. Edman sequencing proved that the sequences obtained for these proteins all originated from the N-terminus, however given other results observed, C-terminal truncation cannot be excluded. Subsequent analysis of βTC6-F7 granules by 2-DE confirmed the presence of ubiquitin and calreticulin, with both proteins migrating at the expected MW for the whole protein (data not shown). The combination of MALDI-TOF MS and N-terminal sequencing allowed the unequivocal identification of all remaining peptides (Table 1). Of most interest the peptide herein referred to as vesiculin.

TABLE 1

Identification of Proteins Derived From Fractions Enriched in Secretory Granules Table I shows results from N-terminal sequencing and MALDI-TOF mass spectrometry of major RP-HPLC peaks (note: X denotes unidentified residues, HPLC fraction numbers refer to the peaks in FIG. 1B, all MALDI-TOF mass data generated in linear mode).

| HPLC Fraction | N-terminal Sequence | Protein Identified | Fragment Location | Average molecular mass Observed | Calculated | Organelle Origin |
|---|---|---|---|---|---|---|
| 1 | EVEDPQVE [SEQ ID NO: 30] | C peptide I | 1-21 | 2239.4 | 2240.4 | S.G.[b] |
| 2 | EVEDPQVA [SEQ ID NO: 31] | C-peptide II | 1-22 | 2178.4 | 2179.3 | S.G. |
| 2 | EVEDPQVA [SEQ ID NO: 32] | C peptide II | 1-23 | 2279.0 | 2280.4 | S.G. |
| 3 | EVEDPQVA [SEQ ID NO: 33] | C peptide II | 1-21 | 2071.5[a] | 2051.2 | S.G. |
| 4 | EVED [SEQ ID NO: 34] | C peptide II | 1-24 | 2393.4 | 2393.6 | S.G. |
| 5 | DVSTSQAV [SEQ ID NO: 35] | ProIGF-II | 69-89 | 2337.3 | 2338.6 | S.G. |
| 6 | EVED [SEQ ID NO: 36] | C Peptide II | 1-26 | 2599.8[a] | 2577.8 | S.G. |
| 7 | (A)YGPGETF/ [SEQ ID NO: 37]; GIVEEXXF [SEQ ID NO: 38] | Vesiculin | Des(37-40) IGF-II | 6851.1 6782.5 | 6847.6 6776.6 | S.G. |
| 7 | DVSTSQAV [SEQ ID NO: 39] | ProIGF-II (Preptin) | 69-102 | 3949.0 | 3948.4 | S.G. |
| 8 | MQIFVKTL [SEQ ID NO: 40] | Ubiquitin | 1- | — | — | Cyt[c] & E.R.[d] |
| 9 | K-NTA [SEQ ID NO: 41] | Amylin | Whole molecule | 3921.5 | 3921.4 | S.G. |

TABLE 1-continued

Identification of Proteins Derived From Fractions Enriched in Secretory Granules Table I shows results from N-terminal sequencing and MALDI-TOF mass spectrometry of major RP-HPLC peaks (note: X denotes unidentified residues, HPLC fraction numbers refer to the peaks in FIG. 1B, all MALDI-TOF mass data generated in linear mode).

| HPLC Fraction | N-terminal Sequence | Protein Identified | Fragment Location | Average molecular mass Observed | Calculated | Organelle Origin |
|---|---|---|---|---|---|---|
| 10 | XVKQHLXGPHLV/[SEQ ID NO: 42]; XIVDQXXTSIXX [SEQ ID NO: 43] | Insulin I | Whole molecule | 5802.4 | 5803.7 | S.G. |
| 11 | FVKQHLXGSHLV/ [SEQ ID NO: 44]; GIVDQXXTSIXS [SEQ ID NO: 45] | Insulin II | Whole molecule | 5795.4 | 5796.7 | S.G. |
| 12 | YPSKPDNP [SEQ ID NO: 46] | Neuropeptide Y | 1- | — |  | S.G. |
| 13 | KPVNSPMT [SEQ ID NO: 47] | Chromogranin A | 1- | — |  | S.G. |
| 14 | DPAIYFKE [SEQ ID NO: 48] | Calreticulin | 1- | — |  | E.R. |

Figure 2A:
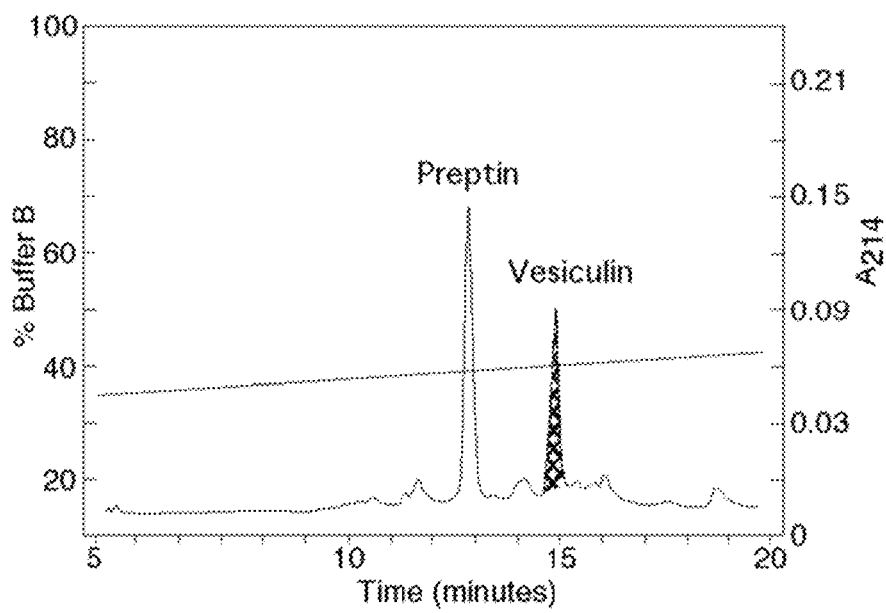
Figure 2B:
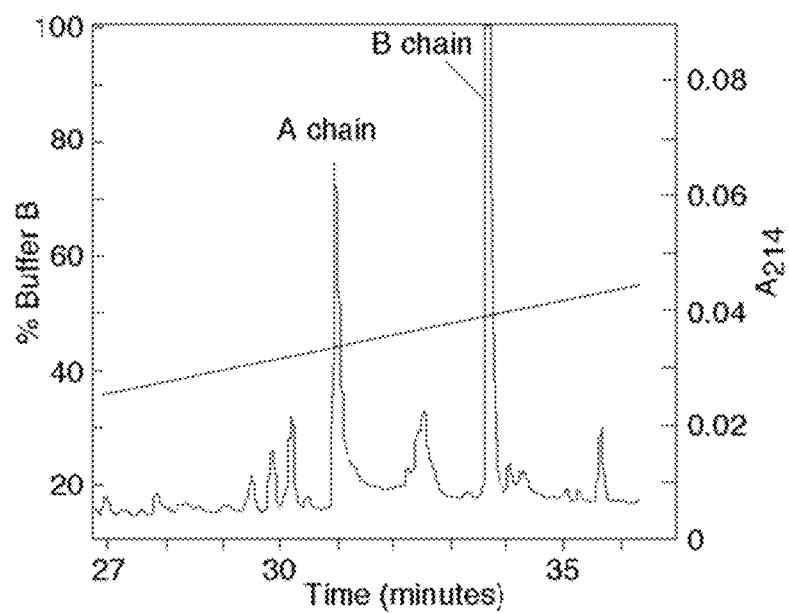

$^a$m/z for Na$^+$ adduct, subtract 22 for protonated species.
$^b$S.G. = secretory granule
$^c$Cyt. = cytosol
$^d$E.R. = endoplasmic reticulum The IGF-II variant isolated from O-cell secretory granules—The major peak that eluted immediately before insulin-I (hatched peak in FIG. 1B) was subjected to further RP-HPLC (FIG. 2A) and was found to consist of two closely eluting peaks. The first peak was identified as preptin, a novel peptide derived from the E-peptide of proIGF-II. The second hatched peak was subjected to MALDI-TOF MS and N-terminal sequencing and found to consist of two closely related IGF-II variants with molecular masses (M+H$^+$) of 6852.1 and 6783.5 Da (FIG. 2A and Table 1). These variants differed only by the absence of the N-terminal alanine in one molecule, a common phenomenon observed for rat IGF-II sequences (Yang, et al., *J. Biol. Chem.* 260:2578-2582 (1985)). These two moieties were so closely related it was impossible to further separate them by chromatographic means (data not shown), and all subsequent investigations were carried out on the protein pair. For simplicity only report on information for the N-terminally intact molecule is reported. N-terminal sequencing yielded a double sequence suggesting that these molecules most likely consisted of two chains. The purified protein was reduced and alkylated and the resulting peptides were separated by RP-HPLC (FIG. 2B), prior to MALDI-TOF MS.

Reduction and Alkylation of Vesiculin—The vesiculin peak was dried by speed-vac concentration and dissolved in 100 μl of tris-buffered GnHCl (6M guanidine-HCl buffered with 300 mM Tris/2 mM EDTA pH 8.8) before the addition of 2 μl of 10% dithiothreitol (DTT). The Eppendorf tube was purged with argon before incubation in the dark for 3-h at 37° C. (waterbath). The reduced product was then alkylated by the addition of 3 μl of iodoacetic acid (1.44M iodoacetic acid in 1M NaOH) incubated in the dark for a further 45-min at room temperature. The alkylation reaction was stopped by the addition of 18 μl 10% DTT. Reduced and alkylated vesiculin was subjected to RP-HPLC purification and MALDI-TOF MS analysis.

Peaks A and B (FIG. 2B) yielded molecular masses of 3181.7 Da and 4014.5 Da respectively, which corresponded closely to the carboxymethylated molecular weights for IGF-II residues G41-E67 and A1-N36 (with expected molecular masses of 3180.3 and 4015.3 respectively). The separate chains were then digested with an asparagine-specific protease, and the resulting peptides were separated by RP-HPLC (FIGS. 2C and D), prior to complete N-terminal protein sequencing (Table 2).

Asp-N Proteolysis of Reduced Vesiculin—vesiculin A and B chains were reduced in volume to approximately 2 μl by speed-vac concentration, before the addition of 100 μl of 50 mM phosphate buffer (pH 8.0). Endoproteinase Asp-N was reconstituted according to supplier's instructions before 6.25 μl (0.25 μg enzyme) was added to each Eppendorf tube and incubated for 2-h at 37° C. (waterbath). Peptides were separated by RP-HPLC and subjected to MALDI-TOF MS.

TABLE 2

Confirmed NH$_2$-sequence of vesiculin fragments after reduction/alkylation and proteolytic digestion with Asp-N

Figure 2C:
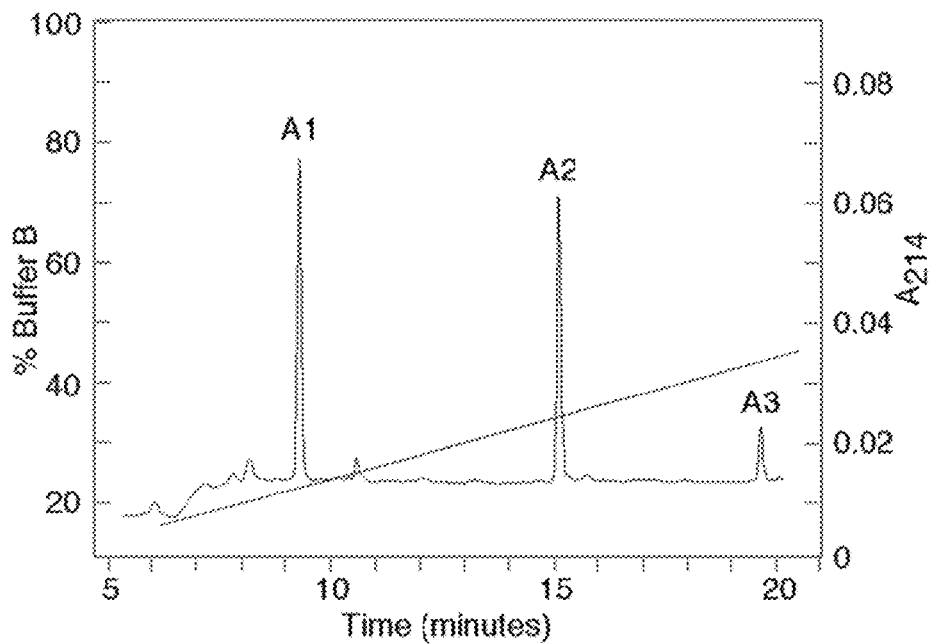
Figure 2D:
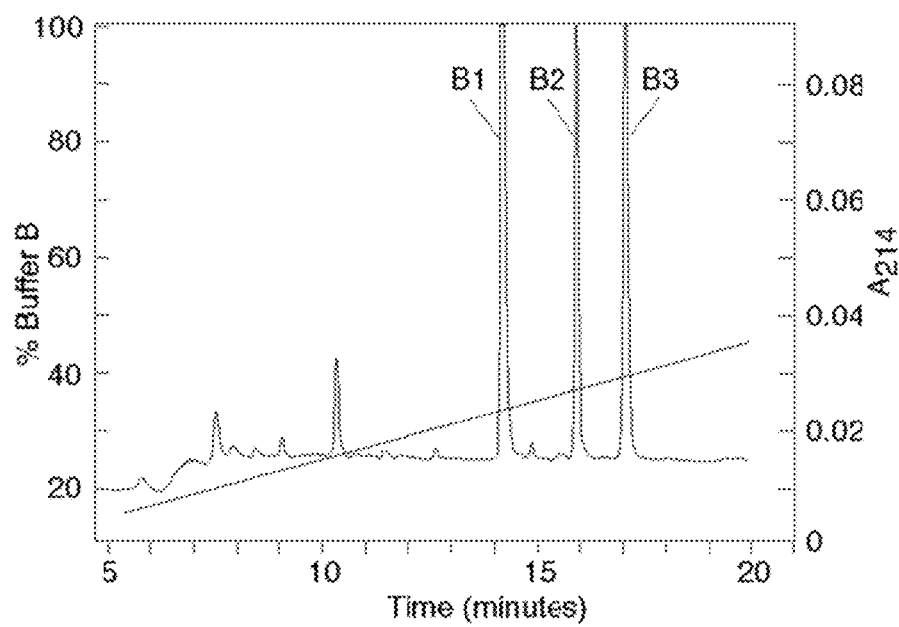

| Figure Description | NH$_2$-Sequence |
|---|---|
| FIG. 2C, A1 | ETYCATPAKSE [SEQ ID NO: 49] |
| FIG. 2C, A2 | GIVEECCFRSC [SEQ ID NO: 50] |
| FIG. 2C, A3 | DLALL [SEQ ID NO: 51] |
| FIG. 2D, B1 | DRGFYFSRPSSRAN [SEQ ID NO: 52] |
| FIG. 2D, B2 | DTLQFVCS [SEQ ID NO: 53] |
| FIG. 2D, B3 | A/YGPGETLCGGELV [SEQ ID NO: 54] |

Figure 3A:
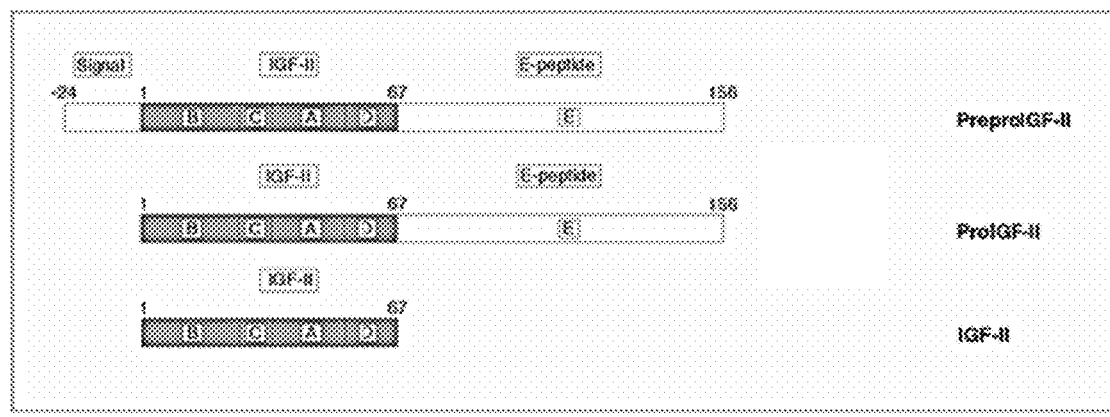
Figure 3B:
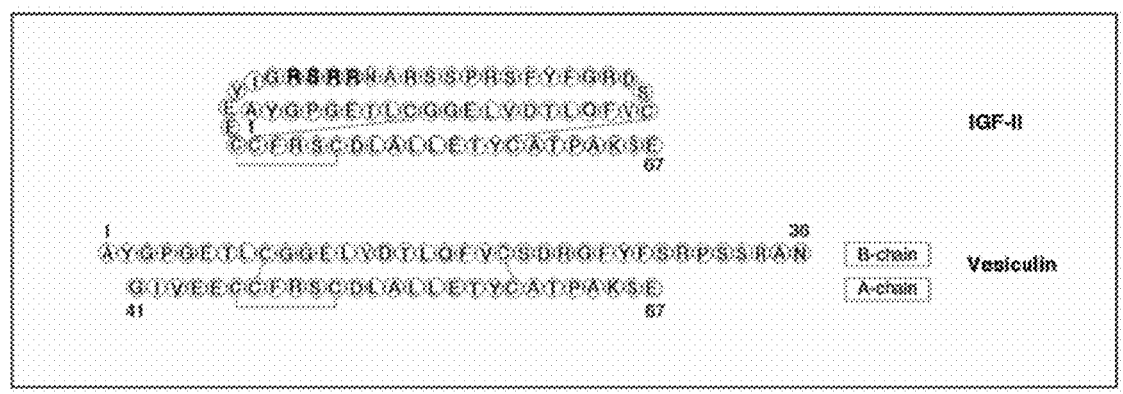

The complete sequence confirmed the identity of a double-chain molecule that corresponds to mature mouse IGF-II with residues R37-R38-S39-R40 removed from the COOH-terminus of the C-domain of IGF-II, while the B, A and D domains remain intact (FIG. 3). It was determined by similarity and mass spectral analysis that the B- and A-chains are held together by disulfide bonds between C9-C47 and C21-C60 (amino acids numbered according to their position in the IGF-II polypeptide), with a further intra chain disulfide bond between C46-051 (FIG. 3). These disulfide bonds can also be designated as being between C9-C43, C21-C56, and C42-C47, respectively, when numbered according to their position in the mature vesiculin peptide.

The primary structure of this peptide, vesiculin, and its sequence relationship to IGF-II is illustrated in FIG. 3.

EXAMPLE 3

This Example describes experiments demonstrating vesiculin bioactivity, here the incorporation of glucose into muscle glycogen. The soleus muscle was dissected from anaesthetized fasted male Wistar rats (200 g±20 g). Each muscle was then teased longitudinally into 3 equal strips with a final radius of approximately 1.5 mm. An average of six muscle strips were transferred into flasks, containing 10 ml of carbogen-saturated nDMEM and peptide (vesiculin, insulin-II, or commercial human IGF-II (GroPep) at concentrations ranging from 0.71 nM to 237 nM, before the addition of 10 µl of (0.5 µCi) D-[$^{14}$C(U)]-Glucose. Flasks were then incubated in a shaking water bath for 120 minutes at 30° C. under a stream of carbogen.

After incubation, the muscle strips were removed and blotted dry before being frozen instantly in liquid nitrogen and freeze-dried for 24 hours. The dried weight of muscle strip was recorded before the muscle strips were solubilised in 250 µl of 60% KOH (70° C. water bath for 45 minutes). 750 µl of ice-cold ethanol was then added and the tubes were left overnight at −20° C. to facilitate glycogen precipitation. Tubes were then centrifuged at 9000 g for 15 minutes at 0° C., the supernatant aspirated and the glycogen pellet resuspended in 750 µl of ice-cold ethanol. The centrifugation, aspiration, and resuspension steps were repeated twice more before the supernatant was finally aspirated and the glycogen pellets oven-dried at 70° C. for 2 hours. The glycogen pellet was then dissolved in 200 µl of MilliQ water and transferred to a scintillation tube before the addition of 1.8 ml of Starscint scintillant (Hewlett Packard). The tubes were mixed thoroughly, and then counted using a Beckman LS 3801 β-counter. The amount of D-[$^{14}$C(U)]-Glucose incorporation into muscle glycogen was calculated by dividing the cpm values by the dry muscle weight.

To undertake this physiological investigation, we isolated preparative amounts of vesiculin by scaling-up our RP-HPLC purification procedure. We also co-purified insulin-II as a preparative control, and used commercially available human IGF-II as a further positive control. Muscle strips were incubated with in the presence of each peptide and radiolabelled glucose prior to the measurement of glucose incorporation into glycogen.

Figure 4:
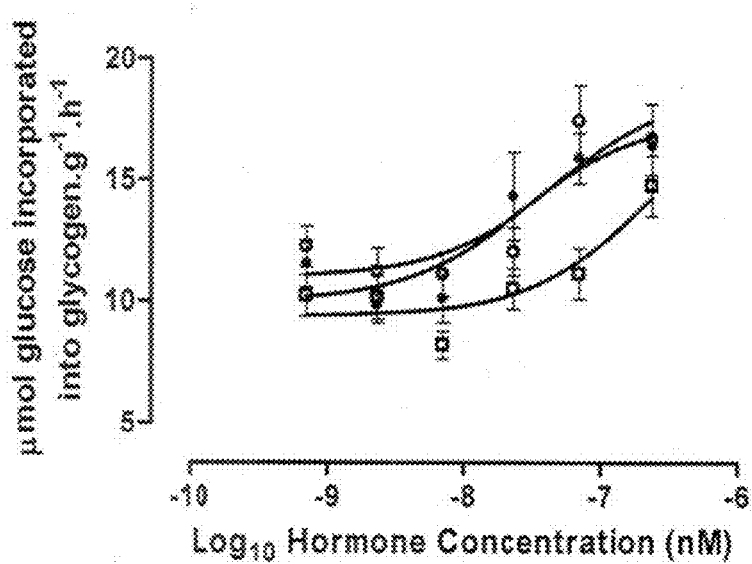

As illustrated in FIG. 4, mouse vesiculin exerted an effect, stimulating the uptake and incorporation of radioactive glucose (EC50: 227 nM, FIG. 4). The positive controls of mouse insulin-II and human IGF-II were more effective in this assay system (EC50's: 27 nM and 48 nM respectively).

EXAMPLE 4

This Example describes the recombinant production of a human vesiculin. Other vesiculins may also be prepared using these methods. Using techniques know in the art, a single polynucleotide sequence is prepared having an Asn-Gly site that joins nucleotide sequences coding for the A and B chains of a vesiculin in the following order: B chain-Asn-Gly-Achain (BAGA). Alternatively, an IGF-II encoding polynucleotide may be used as a starting material to prepare a single-chain polynucleotide for the production of vesiculin by site-directed mutagenesis using the Sculptor in vitro mutagenesis system (Amersham) according to manufacturer's instructions. In this procedure, in vitro mutagenesis is used to introduce an Asn-Gly site in place of IGF-II residues 37-40 (Arg-Arg-Ser-Arg (SEQ. ID. NO. 55)), yielding the BAGA sequence.

An Asn-Gly engineered vesiculin vector (pBAGA) suitable for recombinant expression in yeast is prepared using techniques known in the art to introduce the Asn-Gly vesiculin BAGA polynucleotide sequence into the vector in proper reading frame with regulatory elements. Suitable vectors include pRS400 expression vectors available from the ATCC and pESC vectors available from Stratagene, Inc. (San Diego, Calif.). See, e.g., Geiser, J., "Recombinational cloning vectors for regulated expression in *Saccharomyces cerevisiae*," *Biotechniques* 38(3):378, 382 (2005). pESC vectors each contain GAL1 and GAL10 yeast promoters in opposing orientation, and may thus also be used to prepare vesiculin by introducing separate polynucleotides coding for a vesiculin A chain and a vesiculin B chain into the vector for co-expression in a yeast host strain under the control of a repressible promoter. When two polynucleotides are co-expressed, vesiculin production can be confirmed by methods known in the art, for example, immunoprecipitation analysis.

The pBAGA vector is then transfected into *Saccharomyces cerevisiae* for recombinant expression of the single chain molecule. Following expression, the single chain molecule is isolated and may be purified using art-known methods. See, e.g., Gill, R., et al., *Protein Eng.* 11:1011-1019 (1996). The two-chain vesiculin molecule is then prepared by removing the Asn-Gly linker by hydroxylamine cleavage. Hydroxylamine Asn-Gly linker cleavage is carried out by incubating target protein at 45° C. for 4 h in 2 M hydroxylamine, 0.2M Tris-HCl at pH 9.2. The reaction is terminated by adjusting the pH to <6.0 with concentrated HCl. The protein is then desalted. Cleavage at the junctions of the A- and B-chains may be confirmed by N-terminal sequencing.

From the foregoing, it will be appreciated that, although specific embodiments of the invention have been described herein for the purpose of illustration, various modifications may be made without deviating from the spirit and scope of the invention. The foregoing description is intended to illustrate and not limit the scope of the invention. Accordingly, the present invention is not limited except as by the appended claims.

All patents, patent applications, publications, scientific articles, web sites, and other documents and materials referenced or mentioned herein are indicative of the levels of skill of those skilled in the art to which the inventions pertain, and each such referenced document and material is hereby incorporated by reference to the same extent as if it had been incorporated by reference in its entirety individually or set forth herein in its entirety. The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent. Applicants reserve the right to physically incorporate into this specification any and all materials and information from any such patents, applications, publications, scientific articles, web sites, electronically available information, and other referenced materials or documents.

The specific methods and compositions described herein are representative of preferred embodiments and are exemplary and not intended as limitations on the scope of the inventions. Other objects, aspects, and embodiments will occur to those skilled in the art upon consideration of this specification, and are encompassed within the spirit of the inventions as defined by the scope of the claims. It will be readily apparent to one skilled in the art that varying substitutions and modifications may be made to the inventions disclosed herein without departing from the scope and spirit of the inventions. The inventions illustratively described herein suitably may be practiced in the absence of any element or elements, or limitation or limitations, which is not specifically disclosed herein as essential. Thus, for example, in each instance herein, in embodiments or examples of the present inventions, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically or otherwise expressly disclosed herein. Under no circumstances may the patent be interpreted to be limited by any statement made by any Examiner or any other official or employee of the Patent and Trademark Office unless such statement is expressly and specifically, without qualification or reservation, adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. Thus each is to be read as including the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group, which also form a part of the written description. It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention.

SEQUENCE LISTING

```
<160> NUMBER OF SEQ ID NOS: 70

<210> SEQ ID NO 1
<211> LENGTH: 27
<212> TYPE: PRT
<213> ORGANISM: Homo sapiens
<220> FEATURE:
<221> NAME/KEY: PEPTIDE
<222> LOCATION: (1)..(27)
<223> OTHER INFORMATION: A chain

<400> SEQUENCE: 1

Gly Ile Val Glu Glu Cys Cys Phe Arg Ser Cys Asp Leu Ala Leu Leu
1               5                   10                  15
```

```
Glu Thr Tyr Cys Ala Thr Pro Ala Lys Ser Glu
            20                  25

<210> SEQ ID NO 2
<211> LENGTH: 27
<212> TYPE: PRT
<213> ORGANISM: Artificial
<220> FEATURE:
<223> OTHER INFORMATION: Variant sequence
<220> FEATURE:
<221> NAME/KEY: PEPTIDE
<222> LOCATION: (1)..(27)
<223> OTHER INFORMATION: A Chain
<220> FEATURE:
<221> NAME/KEY: VARIANT
<222> LOCATION: (22)..(22)
<223> OTHER INFORMATION: Thr or Ala

<400> SEQUENCE: 2

Gly Ile Val Glu Glu Cys Cys Phe Arg Ser Cys Asp Leu Ala Leu Leu
1               5                   10                  15

Glu Thr Tyr Cys Ala Glx Pro Ala Lys Ser Glu
            20                  25

<210> SEQ ID NO 3
<211> LENGTH: 27
<212> TYPE: PRT
<213> ORGANISM: Artificial
<220> FEATURE:
<223> OTHER INFORMATION: Variant sequence
<220> FEATURE:
<221> NAME/KEY: Variant
<222> LOCATION: (14)..(14)
<223> OTHER INFORMATION: Ala, Asn, Leu, or a conservative variant of
      either
<220> FEATURE:
<221> NAME/KEY: Variant
<222> LOCATION: (15)..(15)
<223> OTHER INFORMATION: Leu, Ile, or a conservative variant of either
<220> FEATURE:
<221> NAME/KEY: Variant
<222> LOCATION: (18)..(18)
<223> OTHER INFORMATION: Thr, Gln, or a conservative variant of either
<220> FEATURE:
<221> NAME/KEY: Variant
<222> LOCATION: (22)..(22)
<223> OTHER INFORMATION: Thr, Ala, Lys, Val, or a conservative variant
      of either
<220> FEATURE:
<221> NAME/KEY: Variant
<222> LOCATION: (23)..(23)
<223> OTHER INFORMATION: Pro, Ser, or a conservative variant of either
<220> FEATURE:
<221> NAME/KEY: Variant
<222> LOCATION: (24)..(24)
<223> OTHER INFORMATION: Ala, Val, Pro, or a conservative variant
      thereof
<220> FEATURE:
<221> NAME/KEY: Variant
<222> LOCATION: (25)..(25)
<223> OTHER INFORMATION: Lys, Glu, or a conservative variant of either,
<220> FEATURE:
<221> NAME/KEY: Variant
<222> LOCATION: (26)..(26)
<223> OTHER INFORMATION: Ser, Ala, or a conservative variant of either
<220> FEATURE:
<221> NAME/KEY: Variant
<222> LOCATION: (27)..(27)
<223> OTHER INFORMATION: Glu,  Ala, or a conservative variant of either

<400> SEQUENCE: 3

Gly Ile Val Glu Glu Cys Cys Phe Arg Ser Cys Asp Leu Glx Glx Leu
1               5                   10                  15
```

Glu Glx Tyr Cys Ala Glx Glx Glx Glx Glx
            20                  25

<210> SEQ ID NO 4
<211> LENGTH: 27
<212> TYPE: PRT
<213> ORGANISM: Homo sapiens

<400> SEQUENCE: 4

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 5
<211> LENGTH: 25
<212> TYPE: PRT
<213> ORGANISM: Homo sapiens

<400> SEQUENCE: 5

Gly Ile Val Glu Glu Cys Cys Phe Arg Ser Cys Asp Leu Ala Leu Leu
1               5                   10                  15

Glu Thr Tyr Cys Ala Thr Pro Ala Lys
            20                  25

<210> SEQ ID NO 6
<211> LENGTH: 25
<212> TYPE: PRT
<213> ORGANISM: Homo sapiens

<400> SEQUENCE: 6

Gly Ile Val Glu Glu Cys Cys Phe Arg Ser Cys Asp Leu Ala Leu Leu
1               5                   10                  15

Glu Thr Tyr Cys Ala Thr Pro Ala Lys
            20                  25

<210> SEQ ID NO 7
<211> LENGTH: 24
<212> TYPE: PRT
<213> ORGANISM: Homo sapiens

<400> SEQUENCE: 7

Gly Ile Val Glu Glu Cys Cys Phe Arg Ser Cys Asp Leu Ala Leu Leu
1               5                   10                  15

Glu Thr Tyr Cys Ala Thr Pro Ala
            20

<210> SEQ ID NO 8
<211> LENGTH: 23
<212> TYPE: PRT
<213> ORGANISM: Homo sapiens

<400> SEQUENCE: 8

Gly Ile Val Glu Glu Cys Cys Phe Arg Ser Cys Asp Leu Ala Leu Leu
1               5                   10                  15

Glu Thr Tyr Cys Ala Thr Pro
            20

<210> SEQ ID NO 9
<211> LENGTH: 22
<212> TYPE: PRT
<213> ORGANISM: Homo sapiens

<400> SEQUENCE: 9

```
Gly Ile Val Glu Glu Cys Cys Phe Arg Ser Cys Asp Leu Ala Leu Leu
1               5                   10                  15

Glu Thr Tyr Cys Ala Thr
            20

<210> SEQ ID NO 10
<211> LENGTH: 21
<212> TYPE: PRT
<213> ORGANISM: Homo sapiens

<400> SEQUENCE: 10

Gly Ile Val Glu Glu Cys Cys Phe Arg Ser Cys Asp Leu Ala Leu Leu
1               5                   10                  15

Glu Thr Tyr Cys Ala
            20

<210> SEQ ID NO 11
<211> LENGTH: 35
<212> TYPE: PRT
<213> ORGANISM: Homo sapiens

<400> SEQUENCE: 11

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val
        35

<210> SEQ ID NO 12
<211> LENGTH: 34
<212> TYPE: PRT
<213> ORGANISM: Homo sapiens

<400> SEQUENCE: 12

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg

<210> SEQ ID NO 13
<211> LENGTH: 33
<212> TYPE: PRT
<213> ORGANISM: Homo sapiens

<400> SEQUENCE: 13

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser

<210> SEQ ID NO 14
<211> LENGTH: 32
<212> TYPE: PRT
<213> ORGANISM: Homo sapiens

<400> SEQUENCE: 14

Ala Tyr Arg Pro Ser Glu Thr Leu Cys Gly Gly Glu Leu Val Asp Thr
1               5                   10                  15
```

Leu Gln Phe Val Cys Gly Asp Arg Gly Phe Tyr Phe Ser Arg Pro Ala
            20                  25                  30

<210> SEQ ID NO 15
<211> LENGTH: 36
<212> TYPE: PRT
<213> ORGANISM: Mus musculus
<220> FEATURE:
<221> NAME/KEY: PEPTIDE
<222> LOCATION: (1)..(36)
<223> OTHER INFORMATION: B chain

<400> SEQUENCE: 15

Ala Tyr Gly Pro Gly Glu Thr Leu Cys Gly Gly Glu Leu Val Asp Thr
1               5                   10                  15

Leu Gln Phe Val Cys Ser Asp Arg Gly Phe Tyr Phe Ser Arg Pro Ser
            20                  25                  30

Ser Arg Ala Asn
        35

<210> SEQ ID NO 16
<211> LENGTH: 36
<212> TYPE: PRT
<213> ORGANISM: Homo sapiens
<220> FEATURE:
<221> NAME/KEY: PEPTIDE
<222> LOCATION: (1)..(36)
<223> OTHER INFORMATION: B chain

<400> SEQUENCE: 16

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser
        35

<210> SEQ ID NO 17
<211> LENGTH: 36
<212> TYPE: PRT
<213> ORGANISM: Rattus norvegicus
<220> FEATURE:
<221> NAME/KEY: PEPTIDE
<222> LOCATION: (1)..(36)
<223> OTHER INFORMATION: B chain

<400> SEQUENCE: 17

Ala Tyr Arg Pro Ser Glu Thr Leu Cys Gly Gly Glu Leu Val Asp Thr
1               5                   10                  15

Leu Gln Phe Val Cys Ser Asp Arg Gly Phe Tyr Phe Ser Arg Pro Ser
            20                  25                  30

Ser Arg Ala Asn
        35

<210> SEQ ID NO 18
<211> LENGTH: 189
<212> TYPE: DNA
<213> ORGANISM: Mus musculus

<400> SEQUENCE: 18
gcttacggcc ccggagagac tctgtgcgga ggggagcttg ttgacacgct tcagtttgtc      60
tgttcggacc gcggcttcta cttcagcagg ccttcaagcc gtgccaacgg catcgtggaa     120
gagtgctgct tccgcagctg cgacctggcc ctcctggaga catactgtgc cacccccgcc     180

```
aagtccgag                                                             189

<210> SEQ ID NO 19
<211> LENGTH: 189
<212> TYPE: DNA
<213> ORGANISM: Homo sapiens

<400> SEQUENCE: 19
gcttaccgcc ccagtgagac cctgtgcggc ggggagctgg tggacaccct ccagttcgtc    60
tgtggggacc gcggcttcta cttcagcagg cccgcaagcc gtgtgagcgg catcgttgag   120
gagtgctgtt tccgcagctg tgacctggcc ctcctggaga cgtactgtgc taccccccgcc  180 aagtccgag                                                             189

<210> SEQ ID NO 20
<211> LENGTH: 189
<212> TYPE: DNA
<213> ORGANISM: Rattus norvegicus

<400> SEQUENCE: 20
gcttaccgcc ccagcgagac tctgtgcgga ggggagcttg ttgacacgct tcagtttgtc    60
tgttcggacc gcggcttcta cttcagcagg ccttcaagcc gtgccaacgg catcgtggaa   120
gagtgctgct tccgcagctg cgacttggcc ctcctggaga catactgtgc caccccccgcc  180 aagtccgag                                                             189

<210> SEQ ID NO 21
<211> LENGTH: 36
<212> TYPE: PRT
<213> ORGANISM: Bos taurus
<220> FEATURE:
<221> NAME/KEY: PEPTIDE
<222> LOCATION: (1)..(36)
<223> OTHER INFORMATION: B chain

<400> SEQUENCE: 21

Ala Tyr Arg Pro Ser Glu Thr Leu Cys Gly Gly Glu Leu Val Asp Thr
1               5                  10                  15

Leu Gln Phe Val Cys Gly Asp Arg Gly Phe Tyr Phe Ser Arg Pro Ser
            20                  25                  30

Ser Arg Ile Asn
        35

<210> SEQ ID NO 22
<211> LENGTH: 36
<212> TYPE: PRT
<213> ORGANISM: Sheep
<220> FEATURE:
<221> NAME/KEY: PEPTIDE
<222> LOCATION: (1)..(36)
<223> OTHER INFORMATION: B chain

<400> SEQUENCE: 22

Ala Tyr Arg Pro Ser Glu Thr Leu Cys Gly Gly Glu Leu Val Asp Thr
1               5                  10                  15

Leu Gln Phe Val Cys Gly Asp Arg Gly Phe Tyr Phe Ser Arg Pro Ser
            20                  25                  30

Ser Arg Ile Asn
        35

<210> SEQ ID NO 23
<211> LENGTH: 39
```

-continued

```
<212> TYPE: PRT
<213> ORGANISM: Kangaroo
<220> FEATURE:
<221> NAME/KEY: PEPTIDE
<222> LOCATION: (1)..(39)
<223> OTHER INFORMATION: B chain

<400> SEQUENCE: 23

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Leu Pro Gly
            20                  25                  30

Arg Pro Leu Ser Arg Val Ser
            35

<210> SEQ ID NO 24
<211> LENGTH: 36
<212> TYPE: PRT
<213> ORGANISM: Equus sp.
<220> FEATURE:
<221> NAME/KEY: PEPTIDE
<222> LOCATION: (1)..(36)
<223> OTHER INFORMATION: B chain

<400> SEQUENCE: 24

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser
            35

<210> SEQ ID NO 25
<211> LENGTH: 36
<212> TYPE: PRT
<213> ORGANISM: Gallus gallus
<220> FEATURE:
<221> NAME/KEY: PEPTIDE
<222> LOCATION: (1)..(36)
<223> OTHER INFORMATION: B chain

<400> SEQUENCE: 25

Ala Tyr Gly Thr Ala Glu Thr Leu Cys Gly Gly Glu Leu Val Asp Thr
1               5                   10                  15

Leu Gln Phe Val Cys Gly Asp Arg Gly Phe Tyr Phe Ser Arg Pro Val
            20                  25                  30

Gly Arg Asn Asn
            35

<210> SEQ ID NO 26
<211> LENGTH: 37
<212> TYPE: PRT
<213> ORGANISM: Salmon
<220> FEATURE:
<221> NAME/KEY: PEPTIDE
<222> LOCATION: (1)..(37)
<223> OTHER INFORMATION: B chain

<400> SEQUENCE: 26

Glu Val Ala Ser Ala Glu Thr Leu Cys Gly Gly Glu Leu Val Asp Ala
1               5                   10                  15

Leu Gln Phe Val Cys Glu Asp Arg Gly Phe Tyr Phe Ser Arg Pro Thr
            20                  25                  30

Ser Arg Ser Asn Ser
            35
```

```
<210> SEQ ID NO 27
<211> LENGTH: 37
<212> TYPE: PRT
<213> ORGANISM: Eel
<220> FEATURE:
<221> NAME/KEY: PEPTIDE
<222> LOCATION: (1)..(37)
<223> OTHER INFORMATION: B chain

<400> SEQUENCE: 27

Asp Ala Gly Ser Gly Glu Thr Leu Cys Gly Gly Glu Leu Val Asp Ala
1               5                   10                  15

Leu Gln Phe Val Cys Glu Asp Arg Gly Phe Tyr Phe Ser Arg Pro Thr
            20                  25                  30

Ser Arg Ala Asn Ser
        35

<210> SEQ ID NO 28
<211> LENGTH: 37
<212> TYPE: PRT
<213> ORGANISM: Gilthead Bream
<220> FEATURE:
<221> NAME/KEY: PEPTIDE
<222> LOCATION: (1)..(37)
<223> OTHER INFORMATION: B chain

<400> SEQUENCE: 28

Glu Val Ala Ser Ala Glu Thr Leu Cys Gly Gly Glu Leu Val Asp Ala
1               5                   10                  15

Leu Gln Phe Val Cys Glu Asp Arg Gly Phe Tyr Phe Ser Arg Pro Thr
            20                  25                  30

Ser Arg Gly Asn Asn
        35

<210> SEQ ID NO 29
<211> LENGTH: 37
<212> TYPE: PRT
<213> ORGANISM: Shark
<220> FEATURE:
<221> NAME/KEY: PEPTIDE
<222> LOCATION: (1)..(37)
<223> OTHER INFORMATION: B chain

<400> SEQUENCE: 29

Glu Ala Arg Leu Glu Glu Thr Leu Cys Gly Ser Glu Leu Val Asp Thr
1               5                   10                  15

Leu Gln Phe Ile Cys Ala Glu Arg Gly Phe Tyr Phe Val Ser Lys Val
            20                  25                  30

Val Gly Arg Arg Ser
        35

<210> SEQ ID NO 30
<211> LENGTH: 8
<212> TYPE: PRT
<213> ORGANISM: Mus musculus

<400> SEQUENCE: 30

Glu Val Glu Asp Pro Gln Val Glu
1               5

<210> SEQ ID NO 31
<211> LENGTH: 8
<212> TYPE: PRT
<213> ORGANISM: Mus musculus
```

```
<400> SEQUENCE: 31

Glu Val Glu Asp Pro Gln Val Ala
1               5

<210> SEQ ID NO 32
<211> LENGTH: 8
<212> TYPE: PRT
<213> ORGANISM: Mus musculus

<400> SEQUENCE: 32

Glu Val Glu Asp Pro Gln Val Ala
1               5

<210> SEQ ID NO 33
<211> LENGTH: 8
<212> TYPE: PRT
<213> ORGANISM: Mus musculus

<400> SEQUENCE: 33

Glu Val Glu Asp Pro Gln Val Ala
1               5

<210> SEQ ID NO 34
<211> LENGTH: 4
<212> TYPE: PRT
<213> ORGANISM: Mus musculus

<400> SEQUENCE: 34

Glu Val Glu Asp
1

<210> SEQ ID NO 35
<211> LENGTH: 8
<212> TYPE: PRT
<213> ORGANISM: Mus musculus

<400> SEQUENCE: 35

Asp Val Ser Thr Ser Gln Ala Val
1               5

<210> SEQ ID NO 36
<211> LENGTH: 4
<212> TYPE: PRT
<213> ORGANISM: Mus musculus

<400> SEQUENCE: 36

Glu Val Glu Asp
1

<210> SEQ ID NO 37
<211> LENGTH: 8
<212> TYPE: PRT
<213> ORGANISM: Mus musculus

<400> SEQUENCE: 37

Ala Tyr Gly Pro Gly Glu Thr Phe
1               5

<210> SEQ ID NO 38
<211> LENGTH: 8
<212> TYPE: PRT
<213> ORGANISM: Mus musculus
<220> FEATURE:
<221> NAME/KEY: misc_feature
<222> LOCATION: (6)..(7)
```

```
<223> OTHER INFORMATION: Xaa can be any naturally occurring amino acid

<400> SEQUENCE: 38

Gly Ile Val Glu Glu Xaa Xaa Phe
1               5

<210> SEQ ID NO 39
<211> LENGTH: 8
<212> TYPE: PRT
<213> ORGANISM: Mus musculus

<400> SEQUENCE: 39

Asp Val Ser Thr Ser Gln Ala Val
1               5

<210> SEQ ID NO 40
<211> LENGTH: 8
<212> TYPE: PRT
<213> ORGANISM: Mus musculus

<400> SEQUENCE: 40

Met Gln Ile Phe Val Lys Thr Leu
1               5

<210> SEQ ID NO 41
<211> LENGTH: 4
<212> TYPE: PRT
<213> ORGANISM: Mus musculus

<400> SEQUENCE: 41

Lys Asn Thr Ala
1

<210> SEQ ID NO 42
<211> LENGTH: 12
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 42

Xaa Val Lys Gln His Leu Xaa Gly Pro His Leu Val
1               5                   10

<210> SEQ ID NO 43
<211> LENGTH: 12
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 43

Xaa Ile Val Asp Gln Xaa Xaa Thr Ser Ile Xaa Xaa
```

<210> SEQ ID NO 44
<211> LENGTH: 12
<212> TYPE: PRT
<213> ORGANISM: Mus musculus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 44

Phe Val Lys Gln His Leu Xaa Gly Ser His Leu Val
1               5                   10

<210> SEQ ID NO 45
<211> LENGTH: 12
<212> TYPE: PRT
<213> ORGANISM: Mus musculus
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 45

Gly Ile Val Asp Gln Xaa Xaa Thr Ser Ile Xaa Ser
1               5                   10

<210> SEQ ID NO 46
<211> LENGTH: 8
<212> TYPE: PRT
<213> ORGANISM: Mus musculus

<400> SEQUENCE: 46

Tyr Pro Ser Lys Pro Asp Asn Pro
1               5

<210> SEQ ID NO 47
<211> LENGTH: 8
<212> TYPE: PRT
<213> ORGANISM: Mus musculus

<400> SEQUENCE: 47

Lys Pro Val Asn Ser Pro Met Thr
1               5

<210> SEQ ID NO 48
<211> LENGTH: 8
<212> TYPE: PRT
<213> ORGANISM: Mus musculus

<400> SEQUENCE: 48

Asp Pro Ala Ile Tyr Phe Lys Glu
1               5

<210> SEQ ID NO 49
<211> LENGTH: 11
<212> TYPE: PRT
<213> ORGANISM: Mus musculus

<400> SEQUENCE: 49

Glu Thr Tyr Cys Ala Thr Pro Ala Lys Ser Glu
1               5                   10

```
<210> SEQ ID NO 50
<211> LENGTH: 11
<212> TYPE: PRT
<213> ORGANISM: Mus musculus

<400> SEQUENCE: 50

Gly Ile Val Glu Glu Cys Cys Phe Arg Ser Cys
1               5                   10

<210> SEQ ID NO 51
<211> LENGTH: 5
<212> TYPE: PRT
<213> ORGANISM: Mus musculus

<400> SEQUENCE: 51

Asp Leu Ala Leu Leu
1               5

<210> SEQ ID NO 52
<211> LENGTH: 14
<212> TYPE: PRT
<213> ORGANISM: Mus musculus

<400> SEQUENCE: 52

Asp Arg Gly Phe Tyr Phe Ser Arg Pro Ser Ser Arg Ala Asn
1               5                   10

<210> SEQ ID NO 53
<211> LENGTH: 8
<212> TYPE: PRT
<213> ORGANISM: Mus musculus

<400> SEQUENCE: 53

Asp Thr Leu Gln Phe Val Cys Ser
1               5

<210> SEQ ID NO 54
<211> LENGTH: 14
<212> TYPE: PRT
<213> ORGANISM: Mus musculus

<400> SEQUENCE: 54

Ala Tyr Gly Pro Gly Glu Thr Leu Cys Gly Gly Glu Leu Val
1               5                   10

<210> SEQ ID NO 55
<211> LENGTH: 4
<212> TYPE: PRT
<213> ORGANISM: Artificial
<220> FEATURE:
<223> OTHER INFORMATION: consensus

<400> SEQUENCE: 55

Arg Arg Ser Arg
1

<210> SEQ ID NO 56
<211> LENGTH: 36
<212> TYPE: PRT
<213> ORGANISM: Homo sapiens
<220> FEATURE:
<221> NAME/KEY: PEPTIDE
<222> LOCATION: (1)..(36)
<223> OTHER INFORMATION: B chain
<220> FEATURE:
<221> NAME/KEY: VARIANT
<222> LOCATION: (1)..(1)
```

```
<223> OTHER INFORMATION: present or absent

<400> SEQUENCE: 56

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser
        35

<210> SEQ ID NO 57
<211> LENGTH: 36
<212> TYPE: PRT
<213> ORGANISM: Artificial
<220> FEATURE:
<223> OTHER INFORMATION: Variant sequence
<220> FEATURE:
<221> NAME/KEY: PEPTIDE
<222> LOCATION: (1)..(36)
<223> OTHER INFORMATION: B chain
<220> FEATURE:
<221> NAME/KEY: VARIANT
<222> LOCATION: (1)..(1)
<223> OTHER INFORMATION: present or absent
<220> FEATURE:
<221> NAME/KEY: VARIANT
<222> LOCATION: (3)..(3)
<223> OTHER INFORMATION: Gly or Arg
<220> FEATURE:
<221> NAME/KEY: VARIANT
<222> LOCATION: (5)..(5)
<223> OTHER INFORMATION: Gly or Ser
<220> FEATURE:
<221> NAME/KEY: VARIANT
<222> LOCATION: (22)..(22)
<223> OTHER INFORMATION: Gly or Ser
<220> FEATURE:
<221> NAME/KEY: VARIANT
<222> LOCATION: (32)..(32)
<223> OTHER INFORMATION: Ser or Ala
<220> FEATURE:
<221> NAME/KEY: VARIANT
<222> LOCATION: (35)..(35)
<223> OTHER INFORMATION: Ile or Val or Ala
<220> FEATURE:
<221> NAME/KEY: VARIANT
<222> LOCATION: (36)..(36)
<223> OTHER INFORMATION: Asn or Ser

<400> SEQUENCE: 57

Ala Tyr Glx Pro Glx Glu Thr Leu Cys Gly Gly Glu Leu Val Asp Thr
1               5                   10                  15

Leu Gln Phe Val Cys Glx Asp Arg Gly Phe Tyr Phe Ser Arg Pro Glx
            20                  25                  30

Ser Arg Glx Glx
        35

<210> SEQ ID NO 58
<211> LENGTH: 39
<212> TYPE: PRT
<213> ORGANISM: Artificial
<220> FEATURE:
<223> OTHER INFORMATION: Variant sequence
<220> FEATURE:
<221> NAME/KEY: PEPTIDE
<222> LOCATION: (1)..(39)
<223> OTHER INFORMATION: B chain
<220> FEATURE:
<221> NAME/KEY: VARIANT
<222> LOCATION: (1)..(1)
<223> OTHER INFORMATION: absent or is Ala, Glu, Asp, or a conservative
      variant thereof
```

```
<220> FEATURE:
<221> NAME/KEY: VARIANT
<222> LOCATION: (2)..(2)
<223> OTHER INFORMATION: Tyr, Ala, Val, or a conservative variant of
      either
<220> FEATURE:
<221> NAME/KEY: VARIANT
<222> LOCATION: (3)..(3)
<223> OTHER INFORMATION: Arg, Gly, Ala, or a conservative variant
      thereof
<220> FEATURE:
<221> NAME/KEY: VARIANT
<222> LOCATION: (4)..(4)
<223> OTHER INFORMATION: Pro, Thr, Ser, Leu, or a conservative variant
      thereof
<220> FEATURE:
<221> NAME/KEY: VARIANT
<222> LOCATION: (5)..(5)
<223> OTHER INFORMATION: Ser, Gly, Ala, Glu, or a conservative variant
      thereof
<220> FEATURE:
<221> NAME/KEY: VARIANT
<222> LOCATION: (16)..(16)
<223> OTHER INFORMATION: Thr, Tyr, Ala, or a conservative variant
      thereof
<220> FEATURE:
<221> NAME/KEY: VARIANT
<222> LOCATION: (20)..(20)
<223> OTHER INFORMATION: Val, Ile, or a conservative variant thereof
<220> FEATURE:
<221> NAME/KEY: VARIANT
<222> LOCATION: (22)..(22)
<223> OTHER INFORMATION: Gly, Ser, Glu, Ala, or a conservative variant
      thereof
<220> FEATURE:
<221> NAME/KEY: VARIANT
<222> LOCATION: (23)..(23)
<223> OTHER INFORMATION: Asp, Glu, or a conservative variant of either
<220> FEATURE:
<221> NAME/KEY: VARIANT
<222> LOCATION: (29)..(29)
<223> OTHER INFORMATION: Ser, Val, or a conservative variant of either
<220> FEATURE:
<221> NAME/KEY: VARIANT
<222> LOCATION: (30)..(30)
<223> OTHER INFORMATION: Arg, Leu, Ser, or a conservative variant
      thereof
<220> FEATURE:
<221> NAME/KEY: VARIANT
<222> LOCATION: (31)..(31)
<223> OTHER INFORMATION: Pro, Lys, or a conservative variant of either
<220> FEATURE:
<221> NAME/KEY: VARIANT
<222> LOCATION: (32)..(32)
<223> OTHER INFORMATION: Ala, Ser, Gly, Val, Thr, or a conservative
      variant thereof
<220> FEATURE:
<221> NAME/KEY: VARIANT
<222> LOCATION: (33)..(33)
<223> OTHER INFORMATION: Ser, Gly, Val, or a conservative variant
      thereof
<220> FEATURE:
<221> NAME/KEY: VARIANT
<222> LOCATION: (34)..(34)
<223> OTHER INFORMATION: Arg, Pro, Gly, or a conservative variant
      thereof
<220> FEATURE:
<221> NAME/KEY: VARIANT
<222> LOCATION: (35)..(35)
<223> OTHER INFORMATION: Ala, Arg, Val, Ile, Leu, Asn, Ser, Gly, or a
      conservative variant thereof
<220> FEATURE:
<221> NAME/KEY: VARIANT
<222> LOCATION: (36)..(36)
<223> OTHER INFORMATION: Ser, Asn, Arg, or a conservative variant
      thereof
<220> FEATURE:
<221> NAME/KEY: VARIANT
<222> LOCATION: (37)..(37)
<223> OTHER INFORMATION: absent or is Arg, Ser, Asn, or a conservative
```

```
            variant thereof
<220> FEATURE:
<221> NAME/KEY: VARIANT
<222> LOCATION: (38)..(38)
<223> OTHER INFORMATION: absent or is Val, or a conservative variant
      thereof
<220> FEATURE:
<221> NAME/KEY: VARIANT
<222> LOCATION: (39)..(39)
<223> OTHER INFORMATION: absent or is Ser, or a conservative variant
      thereof

<400> SEQUENCE: 58

Glx Glx Glx Glx Glx Gly Thr Leu Cys Gly Gly Glu Leu Val Asp Glx
1               5                   10                  15

Leu Gln Phe Glx Cys Glx Glx Arg Gly Phe Tyr Phe Glx Glx Glx
            20                  25                  30

Glx Glx Glx Glx Glx Glx Glx
        35

<210> SEQ ID NO 59
<211> LENGTH: 27
<212> TYPE: PRT
<213> ORGANISM: Mus musculus
<220> FEATURE:
<221> NAME/KEY: PEPTIDE
<222> LOCATION: (1)..(27)
<223> OTHER INFORMATION: A chain

<400> SEQUENCE: 59

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 60
<211> LENGTH: 27
<212> TYPE: PRT
<213> ORGANISM: Homo sapiens
<220> FEATURE:
<221> NAME/KEY: PEPTIDE
<222> LOCATION: (1)..(27)
<223> OTHER INFORMATION: A chain

<400> SEQUENCE: 60

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 61
<211> LENGTH: 27
<212> TYPE: PRT
<213> ORGANISM: Rattus norvegicus
<220> FEATURE:
<221> NAME/KEY: PEPTIDE
<222> LOCATION: (1)..(27)
<223> OTHER INFORMATION: A chain

<400> SEQUENCE: 61

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 62
<211> LENGTH: 27
```

```
<212> TYPE: PRT
<213> ORGANISM: Bos taurus
<220> FEATURE:
<221> NAME/KEY: PEPTIDE
<222> LOCATION: (1)..(27)
<223> OTHER INFORMATION: A chain

<400> SEQUENCE: 62

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 63
<211> LENGTH: 27
<212> TYPE: PRT
<213> ORGANISM: Sheep
<220> FEATURE:
<221> NAME/KEY: PEPTIDE
<222> LOCATION: (1)..(27)
<223> OTHER INFORMATION: A chain

<400> SEQUENCE: 63

Gly Ile Val Glu Glu Cys Cys Phe Arg Ser Cys Asp Leu Ala Leu Leu
1               5                   10                  15

Glu Thr Tyr Cys Ala Ala Pro Ala Lys Ser Glu
            20                  25

<210> SEQ ID NO 64
<211> LENGTH: 27
<212> TYPE: PRT
<213> ORGANISM: Kangaroo
<220> FEATURE:
<221> NAME/KEY: PEPTIDE
<222> LOCATION: (1)..(27)
<223> OTHER INFORMATION: A chain

<400> SEQUENCE: 64

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 65
<211> LENGTH: 27
<212> TYPE: PRT
<213> ORGANISM: Equus sp.
<220> FEATURE:
<221> NAME/KEY: PEPTIDE
<222> LOCATION: (1)..(27)
<223> OTHER INFORMATION: A chain

<400> SEQUENCE: 65

Gly Ile Val Glu Glu Cys Cys Phe Arg Ser Cys Asp Leu Ala Leu Leu
1               5                   10                  15

Glu Thr Tyr Cys Ala Thr Pro Ala Lys Ser Glu
            20                  25

<210> SEQ ID NO 66
<211> LENGTH: 27
<212> TYPE: PRT
<213> ORGANISM: Gallus gallus
<220> FEATURE:
<221> NAME/KEY: PEPTIDE
<222> LOCATION: (1)..(27)
<223> OTHER INFORMATION: A chain

<400> SEQUENCE: 66
```

Gly Ile Val Glu Glu Cys Cys Phe Arg Ser Cys Asp Leu Ala Leu Leu
1               5                   10                  15

Glu Thr Tyr Cys Ala Lys Ser Val Lys Ser Glu
            20                  25

<210> SEQ ID NO 67
<211> LENGTH: 27
<212> TYPE: PRT
<213> ORGANISM: Salmon
<220> FEATURE:
<221> NAME/KEY: PEPTIDE
<222> LOCATION: (1)..(27)

<400> SEQUENCE: 67

Gly Ile Val Glu Glu Cys Cys Phe Arg Ser Cys Asp Leu Asn Leu Leu
1               5                   10                  15

Glu Gln Tyr Cys Ala Lys Pro Ala Lys Ser Glu
            20                  25

<210> SEQ ID NO 68
<211> LENGTH: 27
<212> TYPE: PRT
<213> ORGANISM: Eel
<220> FEATURE:
<221> NAME/KEY: PEPTIDE
<222> LOCATION: (1)..(27)
<223> OTHER INFORMATION: A chain

<400> SEQUENCE: 68

Gly Ile Val Glu Glu Cys Cys Phe Arg Ser Cys Asp Leu Asn Leu Leu
1               5                   10                  15

Glu Gln Tyr Cys Ala Lys Pro Ala Lys Ser Glu
            20                  25

<210> SEQ ID NO 69
<211> LENGTH: 27
<212> TYPE: PRT
<213> ORGANISM: Gilthead Bream
<220> FEATURE:
<221> NAME/KEY: PEPTIDE
<222> LOCATION: (1)..(27)
<223> OTHER INFORMATION: A chain

<400> SEQUENCE: 69

Gly Ile Val Glu Glu Cys Cys Phe Arg Ser Cys Asp Leu Asn Leu Leu
1               5                   10                  15

Glu Gln Tyr Cys Ala Lys Pro Ala Lys Ser Glu
            20                  25

<210> SEQ ID NO 70
<211> LENGTH: 27
<212> TYPE: PRT
<213> ORGANISM: Shark
<220> FEATURE:
<221> NAME/KEY: PEPTIDE
<222> LOCATION: (1)..(27)
<223> OTHER INFORMATION: A chain

<400> SEQUENCE: 70

Gly Ile Val Glu Glu Cys Cys Phe Arg Ser Cys Asp Leu Leu Ile Leu
1               5                   10                  15

Glu Thr Tyr Cys Ala Val Pro Pro Glu Ala Ala
            20                  25

The invention claimed is:

1. An isolated polypeptide comprising a first chain having the amino acid sequence:

(SEQ ID NO: 1)
Gly Ile Val Glu Glu Cys$_3$ Cys$_4$ Phe Arg Ser Cys$_5$ Asp Leu Ala Leu Leu Glu Thr Tyr Cys$_6$ Ala Thr Pro Ala Lys Ser Glu and a second chain having the amino acid sequence:

(SEQ ID NO: 56)
Ala$_1$ Tyr Arg Pro Ser Glu Thr Leu Cys$_1$ Gly Gly Glu Leu Val Asp Thr Leu Gln Phe Val Cys$_2$ Gly Asp Arg Gly Phe Tyr Phe Ser Arg Pro Ala Ser Arg Val Ser, wherein Ala$_1$ is either present or absent.

2. The isolated polypeptide of claim 1, wherein the first and second chains are joined by one or more disulfide bonds.

3. The isolated polypeptide of claim 2, wherein the first and second chains are joined by two disulfide bonds.

4. A pharmaceutical composition comprising a pharmaceutically acceptable carrier and the polypeptide according to claim 3.

5. A pharmaceutical composition comprising a pharmaceutically acceptable carrier and the polypeptide according to claim 2.

6. A pharmaceutical composition comprising a pharmaceutically acceptable carrier and the polypeptide according to claim 1.

7. The isolated polypeptide of claim 1 wherein said polypeptide has 62 amino acids.

8. The isolated polypeptide of claim 1 wherein said polypeptide has 63 amino acids.

9. The isolated polypeptide of claim 1 wherein said polypeptide is at least about 90% pure.

10. The isolated polypeptide of claim 1, wherein said polypeptide is at least about 95% pure.

* * * * *